(12) United States Patent
Tearney et al.

(10) Patent No.: US 12,310,561 B2
(45) Date of Patent: May 27, 2025

(54) DEVICES, SYSTEMS, AND METHODS FOR ADVANCING AND POSITIONING TETHERED CAPSULE MICROENDOSCOPES

(71) Applicant: The General Hospital Corporation, Boston, MA (US)

(72) Inventors: Guillermo J. Tearney, Cambridge, MA (US); Chulho Daryl Hyun, Cambridge, MA (US); Joseph A. Gardecki, Acton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 18/472,356

(22) Filed: Sep. 22, 2023

(65) Prior Publication Data
US 2024/0074643 A1 Mar. 7, 2024

Related U.S. Application Data

(62) Division of application No. 16/957,314, filed as application No. PCT/US2019/013172 on Jan. 11, 2019, now Pat. No. 11,793,396.
(Continued)

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00126* (2013.01); *A61B 1/00156* (2013.01);
(Continued)

(58) Field of Classification Search
CPC ............ A61B 1/00126; A61B 1/00156; A61B 1/0052; A61B 1/008; A61B 1/041;
(Continued)

(56) References Cited

U.S. PATENT DOCUMENTS 5,025,778 A * 6/1991 Silverstein ......... A61B 1/00078
600/117
5,353,807 A 10/1994 DeMarco
(Continued)

FOREIGN PATENT DOCUMENTS

WO 2017059246 A1 4/2017

OTHER PUBLICATIONS

Gora, M. J., et al. "Tethered capsule endomicroscopy enables less invasive imaging of gastrointestinal tract microstructure." Nature medicine 19.2 (2013): 238-240.
(Continued)

*Primary Examiner* — Aaron B Fairchild
(74) *Attorney, Agent, or Firm* — QUARLES & BRADY LLP

(57) ABSTRACT

In some embodiments, devices, systems, and methods for advancing and positioning tethered capsule microendoscopes are provided. In some embodiments, a device for capsule endomicroscopy is provided, comprising: a tether having a proximal end and distal end; an optical fiber disposed within the tether; a tube enclosing at least a portion of the tether, the tube having a proximal end and a distal end, a diameter of the tube being larger than the diameter of the tether; a housing coupled to the distal end of the tether and the distal end of the tube; and an optical element disposed within the housing, the optical element being optically coupled to the distal end of the optical fiber and configured to direct light received from the optical fiber toward a periphery of the housing.

10 Claims, 14 Drawing Sheets

Related U.S. Application Data

(60) Provisional application No. 62/616,137, filed on Jan. 11, 2018.

(51) Int. Cl.
 *A61B 1/005* (2006.01)
 *A61B 1/008* (2006.01)
 *A61B 1/07* (2006.01)
 *A61B 1/273* (2006.01)
 *A61B 5/00* (2006.01)

(52) U.S. Cl.
 CPC ........ *A61B 1/00172* (2013.01); *A61B 1/0052* (2013.01); *A61B 1/008* (2013.01); *A61B 1/07* (2013.01); *A61B 1/2736* (2013.01); *A61B 5/0073* (2013.01); *A61B 5/0084* (2013.01); *A61B 5/4238* (2013.01); *A61B 1/00078* (2013.01)

(58) Field of Classification Search
 CPC ... A61B 1/07; A61B 1/00078; A61B 1/00172; A61B 1/2736
 See application file for complete search history.

(56) References Cited

U.S. PATENT DOCUMENTS

| | | |
|---|---|---|
| 8,636,651 B2 | 1/2014 | Deal |
| 2006/0195014 A1 | 8/2006 | Seibel |
| 2007/0135683 A1* | 6/2007 | Bob ................... A61B 1/00082 600/114 |
| 2010/0191058 A1 | 7/2010 | Yamazaki |
| 2012/0197241 A1 | 8/2012 | Golden |
| 2012/0253193 A1* | 10/2012 | Hanson ............. A61M 25/0043 604/523 |
| 2013/0289478 A1* | 10/2013 | Kim ................... A61B 1/00078 604/95.04 |
| 2013/0310643 A1 | 11/2013 | Gora |
| 2016/0058268 A1* | 3/2016 | Salman ................ A61B 1/0055 600/149 |
| 2016/0067447 A1 | 3/2016 | Paspa |
| 2016/0276085 A1 | 9/2016 | Matsuki et al. |
| 2018/0160965 A1 | 6/2018 | Tearney |
| 2018/0228374 A1 | 8/2018 | Cui |
| 2019/0029570 A1 | 1/2019 | Stankovic |

OTHER PUBLICATIONS

International Searching Authority. International Search Report and Written Opinion for application PCT/US2019/013172. Mailed on Apr. 24, 2019.

\* cited by examiner

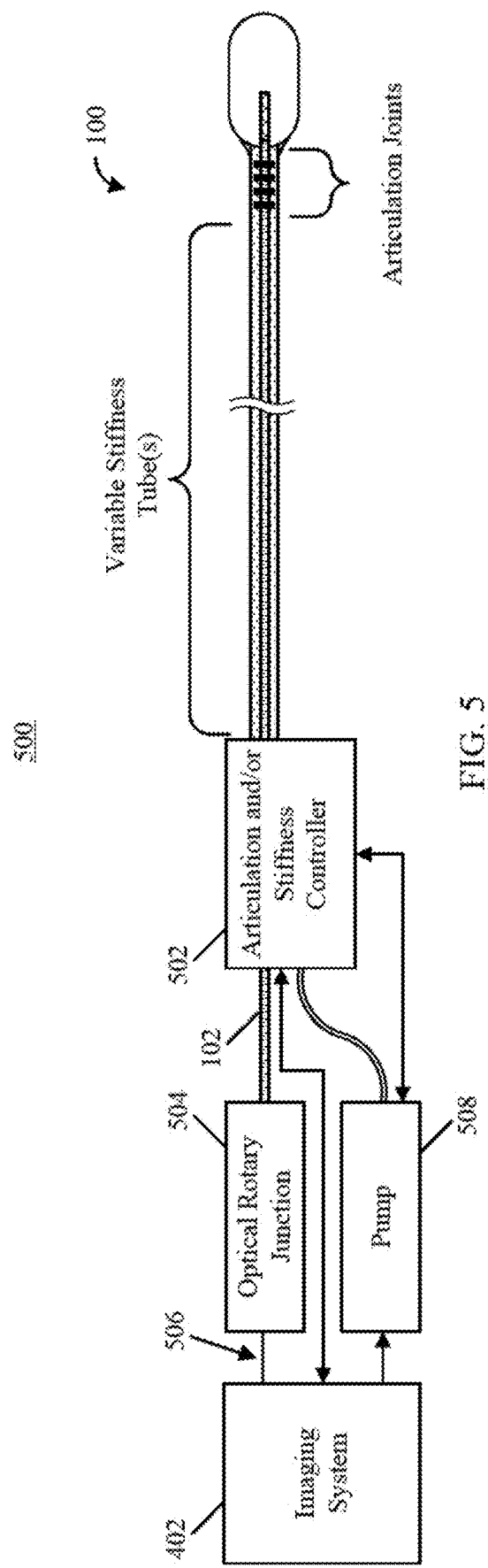

DEVICES, SYSTEMS, AND METHODS FOR ADVANCING AND POSITIONING TETHERED CAPSULE MICROENDOSCOPES

CROSS-REFERENCE TO RELATED APPLICATIONS

This application is a divisional of U.S. application Ser. No. 16/957,314 filed Jun. 23, 2020, which represents the national stage entry of PCT International Application No. PCT/US2019/013172 filed Jan. 11, 2019, which is based on, claims the benefit of, and claims priority to U.S. Provisional Application No. 62/616,137 filed Jan. 11, 2018, the contents of each of which are hereby incorporated herein by reference in their entirety for all purposes.

STATEMENT REGARDING FEDERALLY SPONSORED RESEARCH

N/A

BACKGROUND

Conventional endoscopy techniques can be used to visualize various luminal organs, such as the upper gastrointestinal (GI) tract, in a relatively non-invasive manner. Such techniques generally involve using a flexible video imaging probe that is advanced through a natural orifice and into a luminal organ to be inspected. Such conventional probes, however, while having relatively small diameters (e.g., on the order of 10 to 13 millimeters), have generally the same diameter for the entire length. In addition, the probes must be made so as to accommodate, among other things, a relatively large working channel (which can be used, e.g., to take a biopsy during a procedure). While this diameter is small enough to be inserted without endangering adult subjects, the inserted probe typically causes subjects sufficient discomfort that it is typically necessary to sedate the subject while the procedure is performed. Due to the sedation, such procedures cannot be performed in many clinic settings. Sedation is also expensive (e.g., because it requires additional medical practitioners to administer the sedation, monitor the subject, etc.).

More recently, less invasive capsule endoscopy techniques have been developed for visualization of the GI tract. Such techniques include capsule endoscopy that utilizes a miniaturized camera and a radio transmitter to wirelessly communicate image data to an external device. Another such technique includes tethered capsule endomicroscopy (sometimes referred to as tethered capsule microendoscopy) in which a string-like tether is connected to a capsule with optical and/or electronic transmitters within the tether to communicate signals to and from the capsule. Such capsule-based techniques can be performed without sedation, as they are considerably more comfortable for many adult subjects. However, unlike a conventional gastroscope, such capsules cannot be readily guided through the subject's GI tract. Instead, the subject's digestive system must move the capsule through the GI tract itself (e.g. by peristalsis), which can take a considerable amount of time. For example, tethered capsules having diameters of 8 to 12 millimeters (mm) can take over an hour to reach the duodenum, and in some subjects the capsule never passes the pylorus. Accordingly, although the procedure can be performed without sedation, it is often time consuming and sometimes is unable to image the desired portion of the subject's anatomy.

Accordingly, devices, systems, and methods for advancing and positioning tethered capsule microendoscopes are desirable.

SUMMARY

In accordance with some embodiments of the disclosed subject matter, devices, systems, and methods for advancing and positioning tethered capsule microendoscopes are provided.

In accordance with some embodiments, a device for capsule endomicroscopy is provided, the device comprising: a tether having a proximal end and a distal end, the tether having a first diameter; an optical fiber disposed within the tether, the optical fiber having a proximal end and a distal end; a tube enclosing at least a portion of the tether, the tube having a proximal end and a distal end, the tube having a second diameter that is larger than the first diameter; a housing coupled to the distal end of the tether and the distal end of the tube; and an optical element disposed within the housing, the optical element being optically coupled to the distal end of the optical fiber and configured to direct light received from the optical fiber toward a periphery of the housing.

In some embodiments, the device further comprises: a plurality of articulation joint components, wherein each of the plurality of articulation joint components is disposed adjacent to at least one of the other articulation joints, and each of the plurality of articulation joint components includes at least a first through hole and a second through hole, wherein the first through hole is sized to accommodate the tether; and a wire that passes through the second through hole of each of the plurality of articulation joint components.

In some embodiments, the plurality of articulation joint components further comprises a distal articulation joint component, wherein the distal articulation joint is disposed adjacent to the distal end of the tube, and wherein the wire terminates within the distal articulation joint.

In some embodiments, each of the plurality of articulation joint components is disposed within the tube.

In some embodiments, each of the plurality of articulation joint components is disposed within a distal portion of the tube that is separated from a proximal portion of the tube such that the distal portion of the tube is not in fluid communication with the proximal portion of the tube.

In some embodiments, the device further comprises: a plurality of inner tubes, wherein each of the plurality of inner tubes is disposed within the tube.

In some embodiments, the tube comprises polyethylene terephthalate.

In some embodiments, the optical fiber is configured to rotate within the tether, and the optical fiber is mechanically coupled to the optical element such that the optical element rotates with rotation of the optical fiber.

In some embodiments, the optical element is configured to rotate within the housing, and is mechanically decoupled from the optical fiber.

In some embodiments, free space within the tube is substantially filled by a plurality of individual detached solid particles.

In some embodiments, the tube has a diameter of about 5 millimeters or less.

In some embodiments, the first diameter is no greater than two thirds of the first diameter.

In accordance with some embodiments of the disclosed subject matter, a method for advancing a capsule endomicroscopy device through a luminal structure is provided, the capsule endomicroscopy device comprising a tether having a proximal end and a distal end, the tether having a first diameter, an optical fiber disposed within the tether, the optical fiber having a proximal end and a distal end, a tube enclosing at least a portion of the tether, the tube having a proximal end and a distal end, the tube having a second diameter that is larger than the first diameter, a housing coupled to the distal end of the tether and the distal end of the tube, and an optical element disposed within the housing and configured to direct light received from the optical fiber toward a periphery of the housing, the method comprising: subsequent to the housing entering the luminal structure, causing a first change in pressure within the tube thereby causing a rigidity of the tube to increase; pushing the housing through the luminal structure while the rigidity of the tube has increased to advance the housing through the luminal structure; and subsequent to pushing the housing, causing a second change in pressure within the tube thereby causing the rigidity of the tube to decrease.

In some embodiments, causing the first change in pressure within the tube further comprises causing the first change in pressure within the tube using a pump coupled to the tube to increase pressure within the tube.

In some embodiments, the tube is a first tube, and the capsule endomicroscopy device further comprises a second tube disposed within the first tube, and causing the first change in pressure within the first tube comprises: causing the first change in pressure within the first tube based on using the pump to increase pressure within the second tube.

In some embodiments, free space within the tube is substantially filled by a plurality of individual detached solid particles, and causing the first change in pressure within the tube further comprises: causing the first change in pressure within the tube based on using the pump to decrease pressure within the tube.

In some embodiments, the tube is a first tube, and the capsule endomicroscopy device further comprises a second tube disposed within the tube and substantially filled by a plurality of individual detached solid particles, and causing the first change in pressure comprises causing the pump to decrease pressure within the second tube.

In some embodiments, the capsule endomicroscopy device further comprises a plurality of articulation joint components, wherein each of the plurality of articulation joint components is disposed adjacent to at least one of the other articulation joints, and each of the plurality of articulation joint components includes at least a first through hole and a second through hole, wherein the first through hole is sized to accommodate the tether, and wherein the capsule endomicroscopy device further comprises a wire that passes through the second through hole of each of the plurality of articulation joint components, wherein the method further comprises: retracting the wire thereby causing the plurality of articulation joint components to bend the tube and the tether toward the direction of the wire.

In some embodiments, the optical fiber is configured to rotate within the tether, and the optical fiber is mechanically coupled to the optical element such that the optical element rotates with rotation of the optical fiber, the method further comprising coupling the tether to an optical rotary joint that causes the optical fiber to rotate within the tether while the housing is being pushed through the luminal structure.

In some embodiments, the luminal structure is a stomach of a subject.

In some embodiments, the method further comprises: obtaining structural information from the luminal structure using the optical element, a light source optically coupled to the optical element, and an image sensor optically coupled to the optical element; and generating optical coherence tomography data of the luminal structure based on obtaining the structural information.

In some embodiments, a system for visualizing a luminal organ of a subject is provided, the system comprising: a capsule endomicroscopy device comprising: a tether having a proximal end and a distal end, the tether having a first diameter; an optical fiber disposed within the tether, the optical fiber having a proximal end and a distal end; a tube enclosing at least a portion of the tether, the tube having a proximal end and a distal end, the tube having a second diameter that is larger than the first diameter; a housing coupled to the distal end of the tether and the distal end of the tube; and an optical element disposed within the housing and configured to direct light received from the optical fiber toward a periphery of the housing; an imaging device comprising: an image sensor; and a light source, wherein the optical fiber is optically coupled to the light source and the image sensor; and a pump in fluid communication with at least one lumen of the tube.

In some embodiments, the imaging device is configured to generate optical coherence tomography data.

In some embodiments, the optical fiber is a first optical fiber and is configured to rotate within the tether, the system further comprising: an optical rotary joint coupled to the tether and configured to cause the first optical fiber to rotate within the tether; and a second optical fiber coupled to the optical rotary joint and the imaging device such that the second optical fiber optically couples the light source and the image sensor to the first optical fiber via the optical rotary joint.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 5 shows an example of a system for generating image data using a variable stiffness and articulating tethered capsule endomicroscopy device in accordance with some embodiments of the disclosed subject matter.

DETAILED DESCRIPTION

In accordance with some embodiments of the disclosed subject matter, mechanisms (which can include devices, systems, and methods) for advancing and positioning tethered capsule microendoscopes are provided.

In some embodiments, the mechanisms described herein can utilize a variable stiffness tube or tubes surrounding a tether of a tethered capsule to provide stiffness when desirable to facilitate manual (or automated) advancement of the capsule through a subject's GI tract. For example, a tether having a diameter of about 1 to 3 mm can be surrounded by a polymer tube having a maximum diameter of about 4 to 5 mm. In such an example, when greater pushability is desirable, a pump can be used to increase pressure within the polymer tube which can provide enough rigidity to allow a medical practitioner to manually advance the tether and tube through a portion of a subject's anatomy. By contrast, the tether itself is generally too flexible to be used to push a capsule.

In some embodiments, the mechanisms described herein can utilize a group of articulating joints coupled to a tethered capsule to adjust the direction of a capsule during a procedure. For example, the articulating joints can have a wire passing therethrough such that pulling on the wire causes the joints to bend toward the side of the wire. In such an example, the articulating joints can be used to position a capsule within a relatively large luminal organ (e.g., the stomach) to bring it into closer proximity with a particular portion of a subject's anatomy, thereby providing steerability along with pushability. Such techniques can facilitate imaging particular portions of a subject's anatomy more easily, and can facilitate navigation (e.g., past the pyloric sphincter by moving the capsule toward the pylorus).

Figure 1:
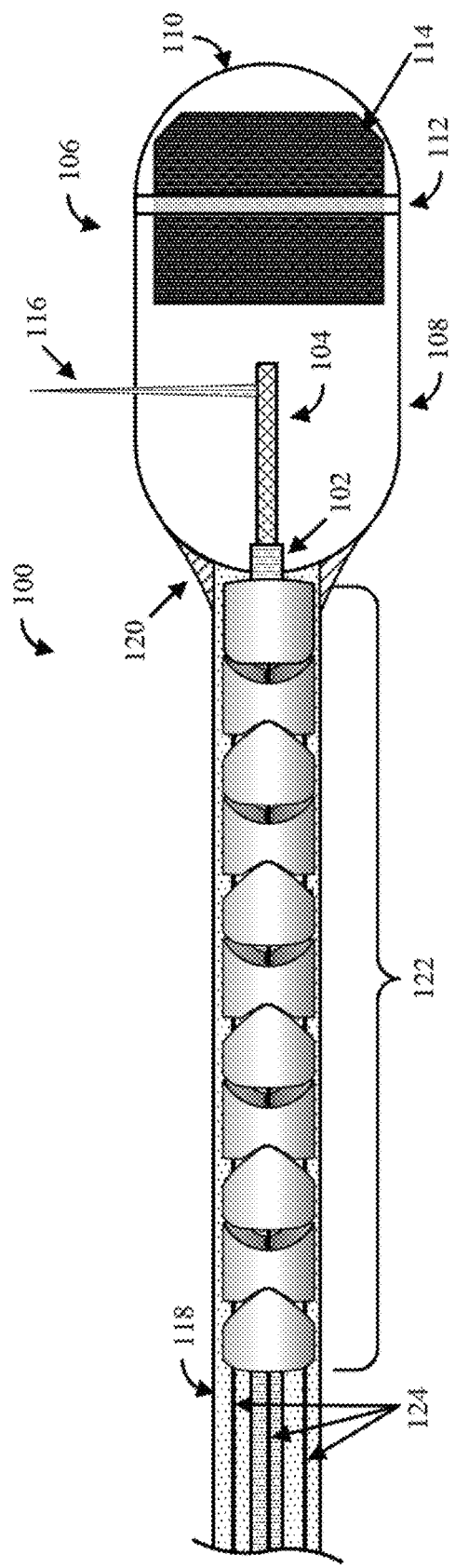
FIG. 1 shows an example of a variable stiffness and articulating tethered capsule endomicroscopy device that can be implemented in accordance with some embodiments of the disclosed subject matter.

FIG. 1 shows an example 100 of a variable stiffness and articulating tethered capsule endomicroscopy device that can be implemented in accordance with some embodiments of the disclosed subject matter. As shown in FIG. 1, device 100 can include a flexible tether 102 which can provide a conduit for an optical fiber (not shown in FIG. 1) that can transmit light to and/or from optics 104 associated with device 100. In some embodiments, tether 102 can be implemented such that the optical fiber can rapidly rotate (e.g., on the order of tens of thousands of revolutions per minute) within tether 102 to cause optics 104 to rotate and direct light toward a periphery of a capsule 106 and a sample (not shown) beyond the capsule 106. Various techniques can be used to implement tethers such as tether 102, some of which are described in U.S. Patent Application Publication No. 2013/0310643, which is hereby incorporated by reference herein in its entirety. Additional techniques that can be used to implement tethers such as tether 102 are described in U.S. Patent Application Publication No. 2006/0195014, which is hereby incorporated by reference herein in its entirety. Alternatively, in some embodiments tether 102 can be implemented such that the optical fiber is statically enclosed within tether 102, and optics 104 are rotated within capsule 106 using other techniques (e.g., using a motor within capsule 106 that is mechanically coupled to optics 104 such that rotation of the motor causes optics 104 to rotate about the longitudinal axis of tether 102). Various techniques can be used to implement a static tether, some of which are described in U.S. Patent Application Publication No. 2018/0160965, which is hereby incorporated by reference herein in its entirety. In some embodiments, tether 102 can be about 1 to 3 millimeters (mm) in diameter, and can have a length of about 500 to 6,000 mm. In some embodiments, optics 104 can include any suitable optical element or combination of elements to cause light transmitted via the optical fiber to be directed toward a periphery of capsule 106. For example, optics 104 can include a ball lens that receives light from the optical fiber and directs light toward the periphery of capsule 106. As another example, optics 104 can include a prism that directs light toward the periphery of capsule 106. As yet another example, optics 104 can include an angled optical element with a reflective surface that directs light toward the periphery of capsule 106. Some examples of such optical elements are described in U.S. Patent Application Publication Nos. 2013/0310643 and 2018/0228374, and in U.S. patent application Ser. No. 16/049,362, filed Jul. 30, 2018. Each of the patent applications referenced in the preceding sentence is hereby incorporated by reference herein in its entirety.

In some embodiments, capsule 106 can include a proximal portion 108 and a distal portion 110, which can be combined to form capsule 106. For example, in some embodiments, proximal portion 108 and distal portion 110 can overlap in a region 112, and can be affixed with an adhesive. In some embodiments, capsule 106 can be about 8 to 12 mm in diameter, and can have a length of about 20 to 35 mm.

In some embodiments, device 100 can include a digital camera 114 that can be used to generate images using conventional digital imaging techniques. For example, digital camera 114 can include an image sensor (e.g., a CCD sensor, a CMOS sensor), focusing optics, a processor, a transmitter, etc. In some embodiments, digital camera 114 can be associated with one or more light sources that emit light in the visible and/or infrared portion of the electromagnetic spectrum. Such light sources can be used to illuminate a sample to be imaged through distal portion 110.

In some embodiments, device 100 can be used to generate image data via tether 102 and optics 104 by transmitting light via the optical fiber within tether 102 which can be focused by optics 104 to generate a beam 116 that can be used to interrogate a sample. In some embodiments, optics 104 can be used to implement any suitable type of microscopy and/or spectroscopy, such as optical coherence tomography (OCT) and related modalities (e.g., optical frequency domain imaging (OFDI), and spectral domain OCT (SD-OCT), time domain OCT), confocal microscopy, spectrally-encoded confocal microscopy (SECM), two photon microscope, second harmonic microscopy, third harmonic microscope, coherent anti-Stokes-Raman spectroscopy (CARS), stimulated Raman scattering (SRS), etc. In some embodiments, tether 102 can have a relatively small diameter. For example, tether 102 can have a diameter of about 1 mm to 3 mm. Tethers with a smaller diameter (e.g., on the order of 1 mm) are generally more easily tolerated by a subject during a procedure. However, it may be more difficult to fabricate small diameter tethers that can accommodate a rotating fiber and additional components (e.g., one or more wires, one or more lumens, etc.).

In some embodiments, tether 102 can be enclosed within a catheter 118, which can be coupled to capsule 106 at a distal portion. In some embodiments, catheter 118 can be coupled to proximal portion 108 of capsule 106 via an adhesive 120. In some embodiments, adhesive 120 can act as a strain relief component. In some embodiments, catheter 118 can be implemented using any suitable material or materials. For example, in some embodiments, catheter 118 can be implemented using polyethylene terephthalate (PET) medical heat shrink tubing. In some embodiments, catheter 118 can be coated with a hydrophilic coating, which can reduce surface friction and facilitate navigation of device 100 during a procedure (e.g., within a subject's gastrointestinal tract).

In some embodiments, the flexibility and/or stiffness of catheter 118 can be adjusted by changing the amount of gas and/or liquid that is contained within catheter 118. For example, in some embodiments, catheter 118 can be coupled to a pump (e.g., at or near a proximal end of catheter 118) which can be used to increase the amount of gas and/or liquid within catheter 118 thus increasing the pressure exerted on an external wall of catheter 118 and increasing the stiffness of catheter 118. As another example, catheter 118 can enclose additional tubes that can be coupled individually and/or collectively to a pump (e.g., at or near proximal end of catheter 118) which can be used to increase the amount of gas and/or liquid within the additional tubes, which can in turn provide mechanical support to an external wall of catheter 118 thus increasing the stiffness of catheter 118. As yet another example, catheter 118 (and/or one or more tubes contained in catheter 118) can be at least partially filled with particles, and catheter 118 can be coupled to a pump (e.g., at or near a proximal end of catheter 118) which can be used to decrease the amount of gas and/or liquid within catheter 118. In such an example, when gas and/or liquid is evacuated from catheter 118, the particles can become more tightly packed together which can increase the rigidity of catheter 118. In some embodiments, any suitable type or types of particles with any suitable diameter can be used to at least partially fill catheter 118, such as sugar, salt (e.g., table salt), titanium dioxide particles, barium sulfate particles, microbeads (e.g., made from glass and/or plastic), coffee grounds, artificial sweeteners (e.g., granulated aspartame, granulated aspartame), any other suitable type of particle, or any suitable combination thereof. In some embodiments, catheter 118 can have any suitable diameter that can accommodate tether 102 and/or any other suitable components. For example, catheter 118 can have an exterior diameter of about 3 mm to 5 mm. Catheters with a smaller diameter are generally more easily tolerated by a subject during a procedure, but also can limit the maximum rigidity that can be achieved. For example, as a diameter of the tube and/or wall thickness of the tube increases, rigidity of the tube (with the same internal pressure) also tends to increase. In some embodiments, catheter 118 can have an initial diameter which can increase as pressure within catheter 118 is increased until a deformation limit is reached. In some embodiments, the exterior diameter of catheter 118 can be larger than an exterior diameter of tether 102 to any suitable degree. For example, the exterior diameter of tether 102 can about two thirds of the diameter of catheter 118 or less. As another example, the exterior diameter of tether 102 can about one half of the diameter of catheter 118 or less. As yet another example, the exterior diameter of tether 102 can about one quarter of the diameter of catheter 118 or less.

In some embodiments, any suitable fluid (e.g., gas and/or liquid) can be used to control the pressure within catheter 118. For example, one or more lumens of catheter 118 can be configured to receive water, air (e.g., any suitable combination of molecules that collectively comprise air), other gases, ferrofluid, and/or magnetorheological fluids.

In some embodiments, catheter 118 and/or other lumens included in catheter 118 can deform radially when internal pressure is increased, depending on how the force of the fluid is distributed within the tube(s). In some embodiments, catheter 118 and/or other lumens included in catheter 118 can be configured to reach a deformation limit well below a pressure that would cause the tube to rupture. For example, a thickness of a wall can be configured to provide sufficient mechanical strength to resist rupture at pressures well above a pressure to be applied to stiffen catheter 118. In some embodiments, after any initial radial deformation, increases in internal pressure (e.g., via more pumped air) can result in more rigidity.

In some embodiments, device 100 can include articulation joints 122 that can be used to modify the shape of a distal end of catheter 118. For example, articulation joints 122 can be manipulated to control the relative orientation of capsule 106 with respect to a portion of catheter 118 corresponding to a proximal end of articulation joints 122. In some embodiments, articulation joints 122 can allow a user to control the orientation of capsule 106 along one or more degrees of freedom.

In some embodiments, one or more wires 124 can pass through catheter 118, and can be coupled to articulation joints 122. In such embodiments, wires 124 can be used to control articulation of articulation joints 122. For example, retracting a wire 124 that is coupled to one side of articulation joints 122 can cause articulation joints 122 to bend toward that side, and advancing wire 124 coupled to that side can cause articulation joints 122 to bend away from that side. As another example, pushing a wire 124 that is coupled to one side of articulation joints 122 can cause articulation joints 122 to bend away from that side. In some embodiments, articulation joints 122 can have any suitable dimensions. For example, in some embodiments, components of articulation joints 122 can have an outer diameter of about between about 3.5 to 4.9 mm. In a more particular example, each component of articulation joints 122 has an outer diameter of about 4.5 mm. In some embodiments, the assembly of articulation joints 122 can have any suitable length and/or any suitable number of components. For example, the assembly of articulation joints 122 can be from about 35 mm to 60 mm. Additionally, including a greater number of joint components can facilitate a larger deflection angle. For example, depending on the number and arrangement of joint components, the assembly of articulation joints 122 can have a maximum deflection angle of about 45 to 180 degrees. In the examples described below in connection with FIGS. 11A to 11C, and shown in FIGS. 13A, 13B, and 14, the maximum deflection angle is about 70 degrees with ten joint components. In some embodiments, catheter 118 can be rotated about its longitudinal axis to change an orientation of capsule 106.

In some embodiments, a portion of catheter 118 that has a variable stiffness and the portion of catheter 118 that encloses articulation joints 122 can be compartmentalized such that articulation joints 122 can be actuated regardless of the state of the rest of catheter 118. For example, in some embodiments, at least a portion of articulation joints 122 can be encased in a flexible material that is impervious to fluid, such as fluid of a type that is used to adjust the stiffness of catheter 118. In a more particular example, articulation joints can be encapsulated by a plastic or rubber balloon. In such an example, the material encasing articulation joints 122 can also effectively act as a seal at the distal end of catheter 118. In some embodiments, catheter 118 can be extruded to have multiple lumens, and a lumen used to adjust the stiffness of catheter 118 can be separated from a lumen in which articulation joints 122 are present. In some embodiments, catheter 118 can be assembled from multiple tubes (e.g., arranged concentrically, arranged end to end, or any other suitable arrangement), and a lumen used to adjust the stiffness of catheter 118 can be separated from a lumen in which articulation joints 122 are present.

Figure 2B:
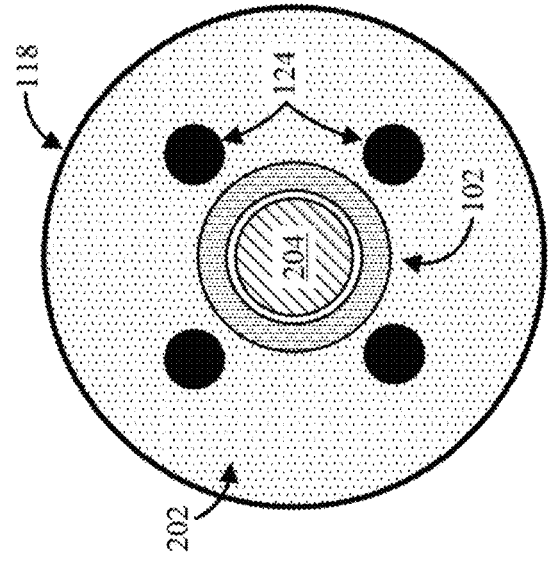
FIG. 2B shows an example of a cross-sectional view of a variable stiffness and articulating catheter that can be used in conjunction with the tethered capsule endomicroscopy device of FIG. 1 in accordance with some embodiments of the disclosed subject matter.
Figure 2A:
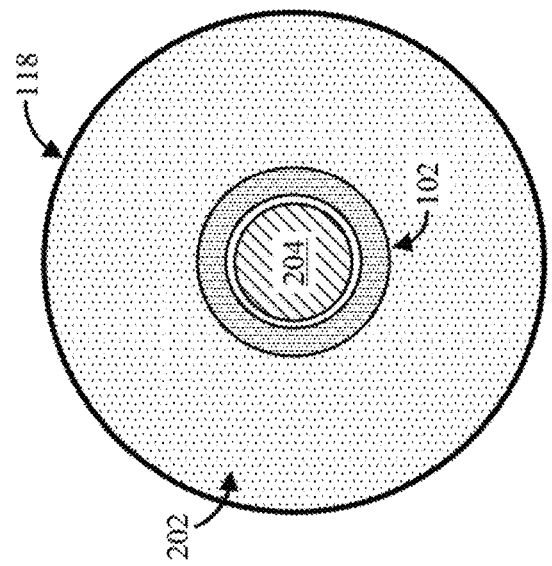
FIG. 2A shows an example of a cross-sectional view of a variable stiffness catheter that can be used in conjunction with the tethered capsule endomicroscopy device of FIG. 1 in accordance with some embodiments of the disclosed subject matter.

FIG. 2A shows an example of a cross-sectional view of a variable stiffness catheter that can be used in conjunction with the tethered capsule endomicroscopy device of FIG. 1 in accordance with some embodiments of the disclosed subject matter. As shown in FIG. 2A, catheter 118 can radially enclose and surround tether 102 and help create a lumen 202, which is defined by an outer surface of tether 102 and an inner surface of catheter 118. In some embodiments, lumen 202 can be coupled to a pump, which can be used to adjust the pressure within lumen 202 (e.g., by pumping fluid into and out of lumen 202) to control the stiffness of catheter 118.

In some embodiments, tether 102 can radially enclose optical fiber 204. Optical fiber 204 can be any suitable type of optical fiber such as a single mode fiber or a multi-mode fiber. Additionally, optical fiber 204 can be associated with any suitable type of cladding (e.g., cladding or dual-cladding).

FIG. 2B shows an example of a cross-sectional view of a variable stiffness and articulating catheter that can be used in conjunction with the tethered capsule endomicroscopy device of FIG. 1 in accordance with some embodiments of the disclosed subject matter. As shown in FIG. 2B, any suitable number of wires 124 can pass through lumen 202. One or more of wires 124 can be used in control of articulation joints 122, while one or more other wires can be used for other purposes, such as providing power and/or control signals to digital camera 114, providing power and/or control signals to a motor associated with optics 104, etc. Note that, while wires 124 are shown as being monolithic to avoid overcomplicating the figures, wires 124 can be implemented using various techniques. For example, one or more of wires 124 can be encased within a sleeve. As another example, one or more of wires 124 can be a cable that includes multiple conductors (e.g., for communication with digital camera 114). Additionally, although wires 124 are depicted as being positioned within lumen 202, but otherwise uncoupled from either tether 102 or catheter 118, this is merely an example, and in some embodiments, one or more of wires 124 can be physically coupled to tether 102 and/or catheter 118 (e.g., to prevent kinking, to prevent the wires from coming into contact with one another, etc.).

Figure 3A:
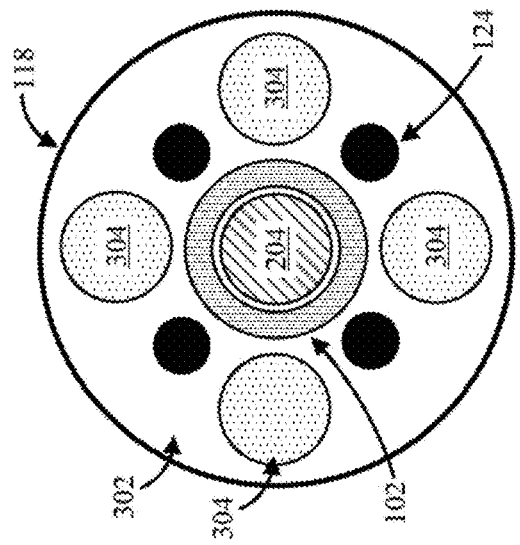
FIG. 3A shows an example of a cross-sectional view of a variable stiffness catheter that includes multiple tubes packed into the catheter that can be used in conjunction with the tethered capsule endomicroscopy device of FIG. 1 in accordance with some embodiments of the disclosed subject matter.

FIG. 3A shows an example of a cross-sectional view of a variable stiffness catheter that includes multiple tubes packed into the catheter that can be used in conjunction with the tethered capsule endomicroscopy device of FIG. 1 in accordance with some embodiments of the disclosed subject matter. As shown in FIG. 3A, an interior 302 of catheter 118 can enclose tether 102 and multiple lumens 304. In some embodiments, each of the lumens 304 can be coupled to a source of fluid (e.g., a pump) collectively or individually. For example, each lumen 304 within catheter 118 can be in fluid communication with the others (e.g., near a proximal end of catheter 118) such that the pressure in the various lumens 304 is at least approximately equal in many circumstances. As another example, one or more lumens 304 can be individually coupled to a source of fluid (e.g., a pump) such that the pressure in each lumen 304 can be individually adjusted. In such an example, pressure in lumens 304 can be adjusted to control the orientation of the distal end of catheter 118 to an extent.

In some embodiments, interior 302 of catheter 118 can be filled (or at least partially filled) with material. For example, interior 302 can be a solid material, such as PET. As another example, interior 302 of catheter 118 can be filled (or partially filled) with solid particles that can be used to provide stiffness by evacuating fluid from interior 302. In such an example, interior 302 can form the walls of lumens 304. In such an example, the particles can be disposed between a wall of catheter 118 and tether 102, and can at least partially surround one or more of lumens 304. Additionally, in such an example, each lumen 304 can be implemented as a separate tube of any suitable material. As still another example, interior 302 of catheter 118 can be filled (or partially filled) with air, water, or any other fluid.

Figure 3B:
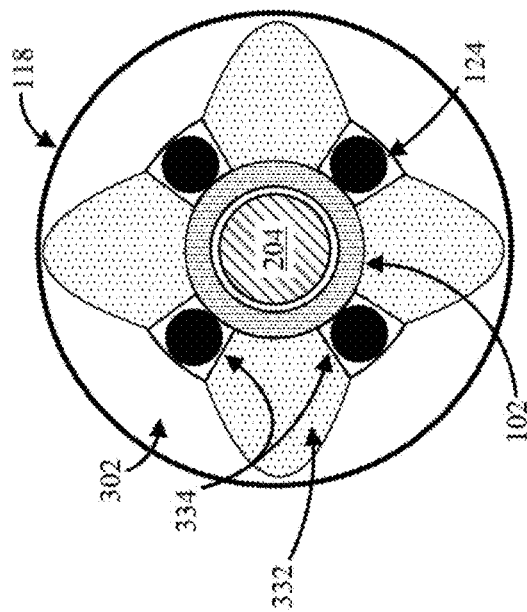
FIG. 3B shows an example of a cross-sectional view of a variable stiffness and articulating catheter that includes multiple packed tubes that can be used in conjunction with the tethered capsule endomicroscopy device of FIG. 1 in accordance with some embodiments of the disclosed subject matter.

FIG. 3B shows an example of a cross-sectional view of a variable stiffness and articulating catheter that includes multiple packed tubes that can be used in conjunction with the tethered capsule endomicroscopy device of FIG. 1 in accordance with some embodiments of the disclosed subject matter. As shown in FIG. 3B, in some embodiments, catheter 118 can include wires 124 which can be used, as described above, to control articulation joints 122, to power and/or communicate with digital camera 114, etc.

Figure 3C:
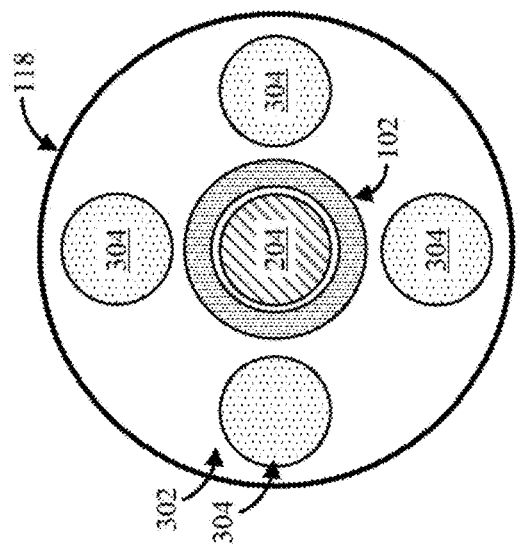
FIG. 3C shows an example of a cross-sectional view of another variable stiffness and articulating catheter that includes multiple packed tubes that can be used in conjunction with the tethered capsule endomicroscopy device of FIG. 1 in accordance with some embodiments of the disclosed subject matter.

FIG. 3C shows an example of a cross-sectional view of another variable stiffness and articulating catheter that includes multiple packed tubes that can be used in conjunction with the tethered capsule endomicroscopy device of FIG. 1 in accordance with some embodiments of the disclosed subject matter. Although four lumens 304 are shown in FIGS. 3A and 3B, this is merely an example, and any suitable number of lumens can be used to adjust the stiffness of catheter 118. For example, as shown in FIG. 3C, three non-spherical lumens 322 can be disposed within catheter 118.

Figure 3D:
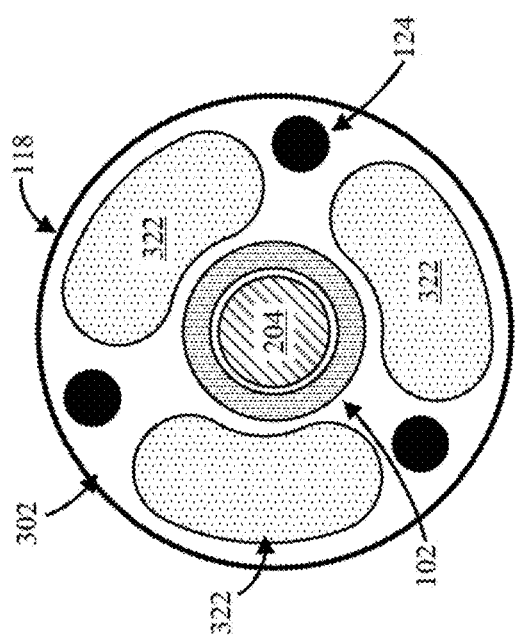
FIG. 3D shows an example of a cross-sectional view of yet another variable stiffness and articulating catheter that includes multiple expandable tubes that can be used in conjunction with the tethered capsule endomicroscopy device of FIG. 1 in accordance with some embodiments of the disclosed subject matter.

FIG. 3D shows an example of a cross-sectional view of yet another variable stiffness and articulating catheter that includes multiple expandable tubes that can be used in conjunction with the tethered capsule endomicroscopy device of FIG. 1 in accordance with some embodiments of the disclosed subject matter. As shown in FIG. 3D, multiple lumens can be coupled to one another within catheter 118, for example, multiple lumens 332 can be formed from a single tube that is compartmentalized (e.g., via ribs 334) such that some compartments can be coupled to a fluid source (e.g., a pump) to adjust stiffness of catheter 118, and other compartments can be used to provide a passage for other components (e.g., wires 124). In some embodiments, lumens 202, 302, 304, 322, and/or 324 can have any suitable dimensions, such as a diameter of about 1 to 5 mm, and a length that is about the same length as the tether (e.g., about 500 to 6,000 mm).

Figure 4A:
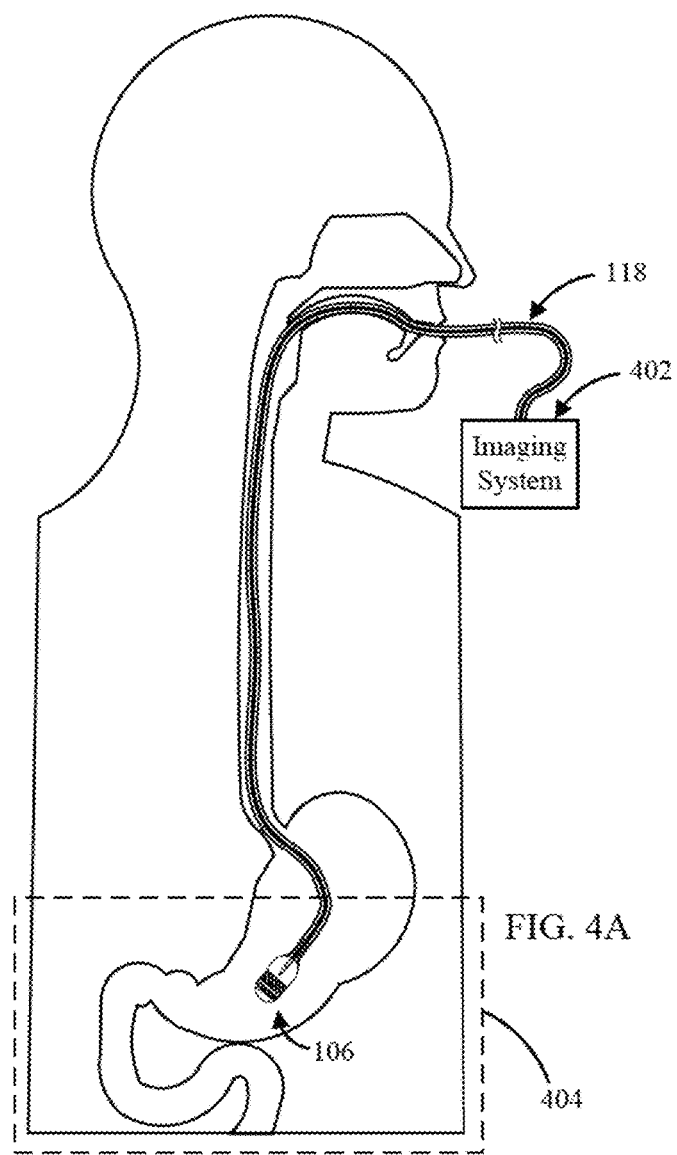
FIG. 4A shows an example of a tethered capsule endomicroscopy device that is inserted into a subject's stomach via the esophagus in accordance with some embodiments of the disclosed subject matter.
Figure 4B:
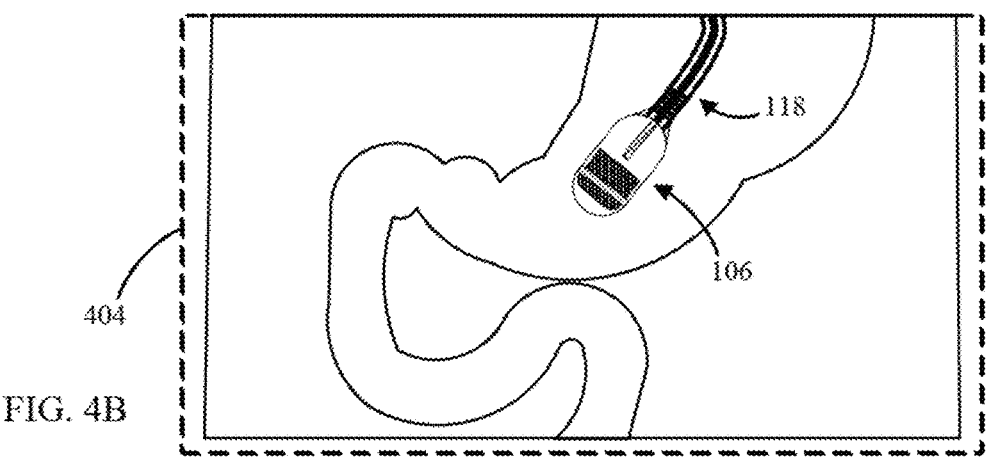
FIG. 4B shows an example of an enlarged view of portion of FIG. 4A.

FIG. 4A shows an example of a tethered capsule endomicroscopy device that is inserted into a subject's stomach via the esophagus in accordance with some embodiments of the disclosed subject matter. As shown in FIG. 4A, capsule 106 is inserted into a subject's stomach via the mouth and esophagus. FIG. 4B shows an example of an enlarged view of portion 404 of FIG. 4A. As shown in FIG. 4A, a proximal end of catheter 118 can be coupled to an imaging system 402, which can be used to generate image data via optics 104 and/or digital camera 114. Additionally, in some embodiments, imaging system 402 can be used to control the pressure within one or more lumens of catheter 118, thereby controlling the stiffness of catheter 118. In some embodiments, imaging system 402 can be used to control articulation joints 122 to adjust the direction of capsule 106 with respect to the subject's anatomy. Such control can be used to position capsule 106 for imaging particular portions of the subject's anatomy, and/or can be used to navigate capsule 106 through the subject's anatomy. For example, the subject can be instruction to swallow capsule 106 while catheter 118 is in a relatively flexible state, and after swallowing a user can increase the stiffness of catheter 118 to advance capsule 106 through the subject's gastrointestinal tract more quickly. As described below, when a subject swallows a conventional capsule it can be advanced via peristalsis into the stomach, and eventually can pass through the pyloric sphincter into the duodenum. However, the amount of time that it takes for the subject to pass the capsule into the duodenum is generally significant (e.g., roughly thirty to eighty minutes and sometimes as much as several hours) and progress can vary widely. In some subjects the capsule may not advance past the pylorus. Accordingly, in some embodiments, after swallowing capsule 106, a user can cause catheter 118 to become more rigid such that the user can push on a portion of catheter 118 to advance capsule 106 more quickly. Additionally, a user can use articulation joints 122 to steer capsule 106 toward a location to which capsule 106 is to be advanced (e.g., toward the pylorus).

FIG. 5 shows an example 500 of a system for generating image data using a variable stiffness and articulating tethered capsule endomicroscopy device in accordance with some embodiments of the disclosed subject matter. As shown in FIG. 5, system 500 can include imaging system 402, and an articulation and/or stiffness controller 502 (hereinafter referred to as controller 502). In some embodiments, controller 502 can be in fluid communication with catheter 118. Additionally, in some embodiments, tether 102 can be coupled to an optical rotary joint 504 that can provide torque to rotate an optical fiber (e.g., optical fiber 204) within tether 102, and optically couple a proximal end of the optical fiber to a light source (e.g., via a static optical fiber 506). In some embodiments, controller 502 can control a pump 508 that is in fluid communication with one or more lumens of catheter 118 to adjust the stiffness of catheter 118. In some embodiments, controller 502 can include one or more mechanical components that can be operated manually, For example, controller 502 can include a valve that can be operated to adjust pressure within catheter 118. As another example, controller 502 can facilitate manual manipulation of wires 124. In some embodiments, controller 502 can be one or more electrical components (e.g., motors, linear actuators, servos, switches, etc.) that can be used to operate one or more mechanical components via signals transmitted from another device. Additionally or alternatively, controller 502 can include one or more electromechanical components that can be operated via signals transmitted from another device.

In some embodiments, controller 502 can be coupled to one or more wires (e.g., wires 124) that can be used to control articulation joints near a distal end of catheter 118. For example, controller 502 can control an actuator (e.g., a linear actuator, a linear servo, or other suitable actuator) coupled to the wire to adjust the position of the wire, and thereby the shape of articulation joints 122.

Figure 6:
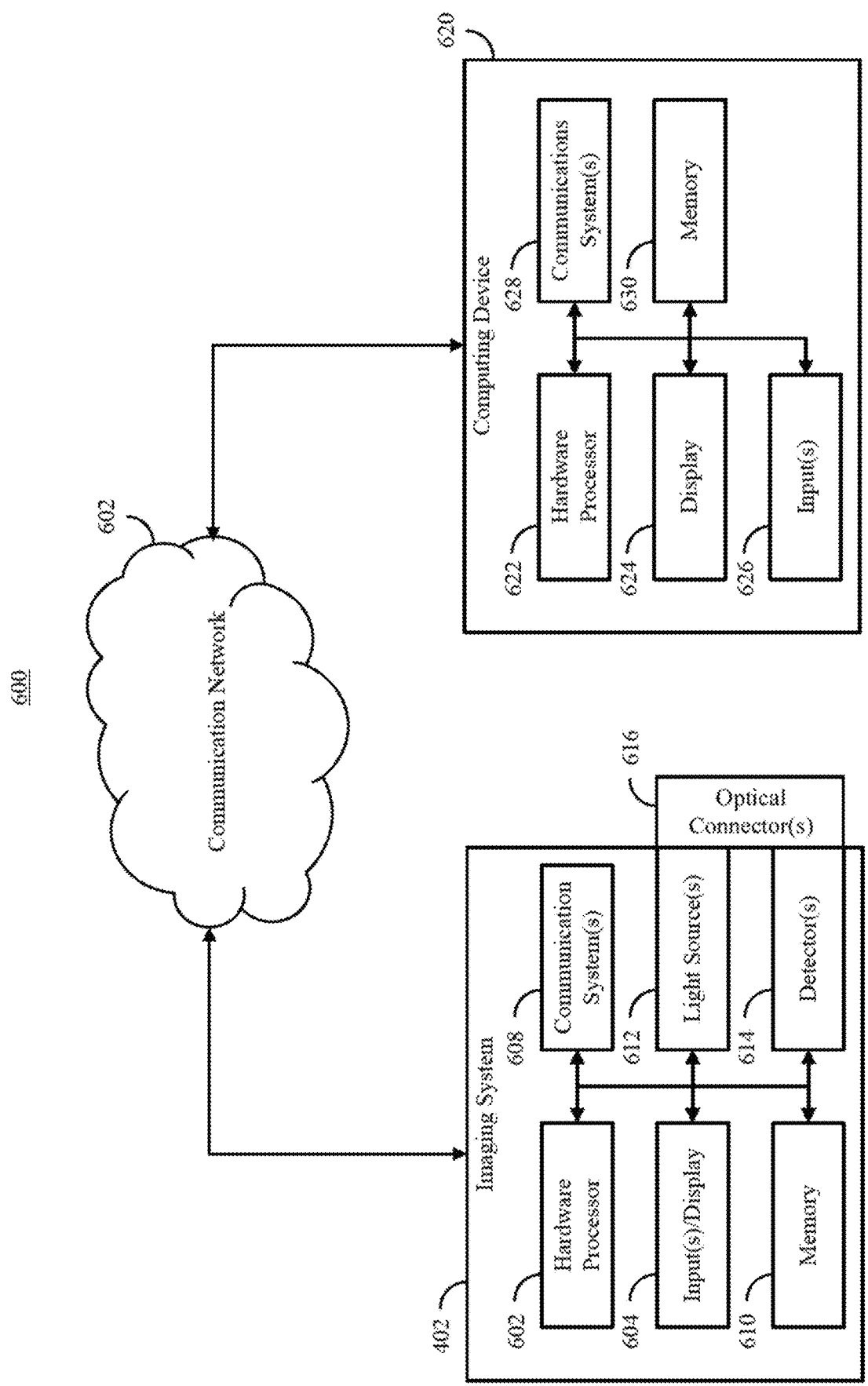
FIG. 6 shows an example of hardware that can be used to implement an imaging device and/or a computing device that can be used in connection with some variable stiffness and articulating tethered capsule endomicroscopy devices that can be implemented in accordance with some embodiments of the disclosed subject matter.

FIG. 6 shows an example 600 of hardware that can be used to implement an imaging device and/or a computing device that can be used in connection with some variable stiffness and articulating tethered capsule endomicroscopy devices that can be implemented in accordance with some embodiments of the disclosed subject matter. As shown in FIG. 6, in some embodiments, imaging system 402 can include a hardware processor 602, a user interface and/or display 604, one or more communication systems 608, memory 610, one or more light sources 612, one or more light detectors 614, and/or one or more optical connectors 616. In some embodiments, hardware processor 602 can be any suitable hardware processor or combination of processors, such as a central processing unit (CPU), a graphics processing unit (GPU), a microcontroller (MCU), a field programmable gate array (FPGA), a dedicated image processor, etc. In some embodiments, input(s) and/or display 604 can include any suitable display device(s), such as a computer monitor, a touchscreen, a television, a transparent or semitransparent display, a head mounted display, etc., and/or input devices and/or sensors that can be used to receive user input, such as a keyboard, a mouse, a touchscreen, a trackball, a joystick, a directional pad, a microphone, a gaze tracking system, motion sensors, etc.

In some embodiments, communications systems 608 can include any suitable hardware, firmware, and/or software for communicating information over a communication network 602 and/or any other suitable communication networks. For example, communications systems 608 can include one or more transceivers, one or more communication chips and/or chip sets, etc. In a more particular example, communications systems 608 can include hardware, firmware and/or software that can be used to establish a Wi-Fi connection, a Bluetooth connection, a cellular connection, an Ethernet connection, an optical connection, etc.

In some embodiments, communication network 602 can be any suitable communication network or combination of communication networks. For example, communication network 602 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 602 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, etc.

In some embodiments, memory 610 can include any suitable storage device or devices that can be used to store instructions, values, etc., that can be used, for example, by hardware processor 602 to process image data generated by one or more optical detectors, to present content using input(s)/display 604, to communicate with a computing device 620 via communications system(s) 608, etc. Memory 610 can include any suitable volatile memory, non-volatile memory, storage, any other suitable type of storage medium, or any suitable combination thereof. For example, memory 610 can include RAM, ROM, EEPROM, one or more flash drives, one or more hard disks, one or more solid state drives, one or more optical drives, etc. In some embodiments, memory 610 can have encoded thereon a computer program for controlling operation of imaging system 402. In some such embodiments, hardware processor 602 can execute at least a portion of the computer program to control one or more light sources and/or detectors, to generate images and/or calculate values (e.g., an OCT image, a conventional digital image, etc.), transmit and/or receive information to/from computing device 620, etc.

In some embodiments, imaging system 402 can include one or more light sources 612, such as narrow band light sources (e.g., a 550 nm laser or light emitting diode, a 650 nm laser or light emitting diode, a superluminescent light emitting diode, etc.) or coherent or incoherent broad band light sources (e.g., a broad band laser configured to sweep various wavelengths, a broadband light emitting diode or combination of light emitting diodes, a white light source, etc.). Additionally, in some embodiments, light sources 612 can be associated with one or more filters.

In some embodiments, imaging system 402 can include one or more light detectors 614, such as one or more photodiodes, and/or one or more image sensors (e.g., a CCD image sensor, a CMOS image sensor). In some embodiments, the image sensor(s) can be a linear array image sensor, a two-dimensional array image sensor, a single pixel image sensor, and/or any other suitable type of image sensor. For example, in some embodiments, detectors 614 can include one or more detectors configured to detect light at specific wavelengths (e.g., using filters, using timing signals, using optics to guide light of different wavelengths to different portions of the detector(s), etc.)

In some embodiments, imaging system 402 can include one or more optical connectors 616. For example, such optical connectors can be fiber optic connectors configured to form an optical connection between light source(s) 612 and/or detector 614 and an optical fiber (e.g., as part of a fiber optic cable).

In some embodiments, computing device 620 can include a hardware processor 622, a display 624, one or more inputs 626, one or more communication systems 628, and/or memory 630. In some embodiments, hardware processor 622 can be any suitable hardware processor or combination of processors, such as a CPU, a GPU, an MCU, an FPGA, a dedicated image processor, etc. In some embodiments, display 624 can include any suitable display devices, such as a computer monitor, a touchscreen, a television, a transparent or semitransparent display, a head mounted display, etc. In some embodiments, inputs 626 can include any suitable input devices and/or sensors that can be used to receive user input, such as a keyboard, a mouse, a touchscreen, a trackball, a joystick, a directional pad, a microphone, a gaze tracking system, motion sensors, etc.

In some embodiments, communications systems 628 can include any suitable hardware, firmware, and/or software for communicating information over communication network 602 and/or any other suitable communication networks. For example, communications systems 628 can include one or more transceivers, one or more communication chips and/or chip sets, etc. In a more particular example, communications systems 628 can include hardware, firmware and/or software that can be used to establish a Wi-Fi connection, a Bluetooth connection, a cellular connection, an Ethernet connection, etc.

In some embodiments, memory 630 can include any suitable storage device or devices that can be used to store instructions, values, etc., that can be used, for example, by hardware processor 622 to present content using display 624, to communicate with one or more imaging devices, etc. Memory 630 can include any suitable volatile memory, non-volatile memory, storage, any other suitable type of storage medium, or any suitable combination thereof. For example, memory 630 can include RAM, ROM, EEPROM, one or more flash drives, one or more hard disks, one or more solid state drives, one or more optical drives, etc. In some embodiments, memory 630 can have encoded thereon a computer program for controlling operation of computing device 620. In such embodiments, hardware processor 622 can execute at least a portion of the computer program to receive content (e.g., image content) from one or more imaging devices (e.g., imaging device 402), present content (e.g., images and/or values,) transmit content to one or more other computing devices and/or imaging systems, etc.

In some embodiments, computing device 620 can be any suitable computing device, such as a general purpose computer or special purpose computer. For example, in some embodiments, computing device 620 can be a smartphone, a wearable computer, a tablet computer, a laptop computer, a personal computer, a server, etc. As another example, in some embodiments, computing device 620 can be a medical device, a system controller (e.g., a system on a chip configured to control a system for performing cryogenic biopsy sampling), etc.

Figure 7:
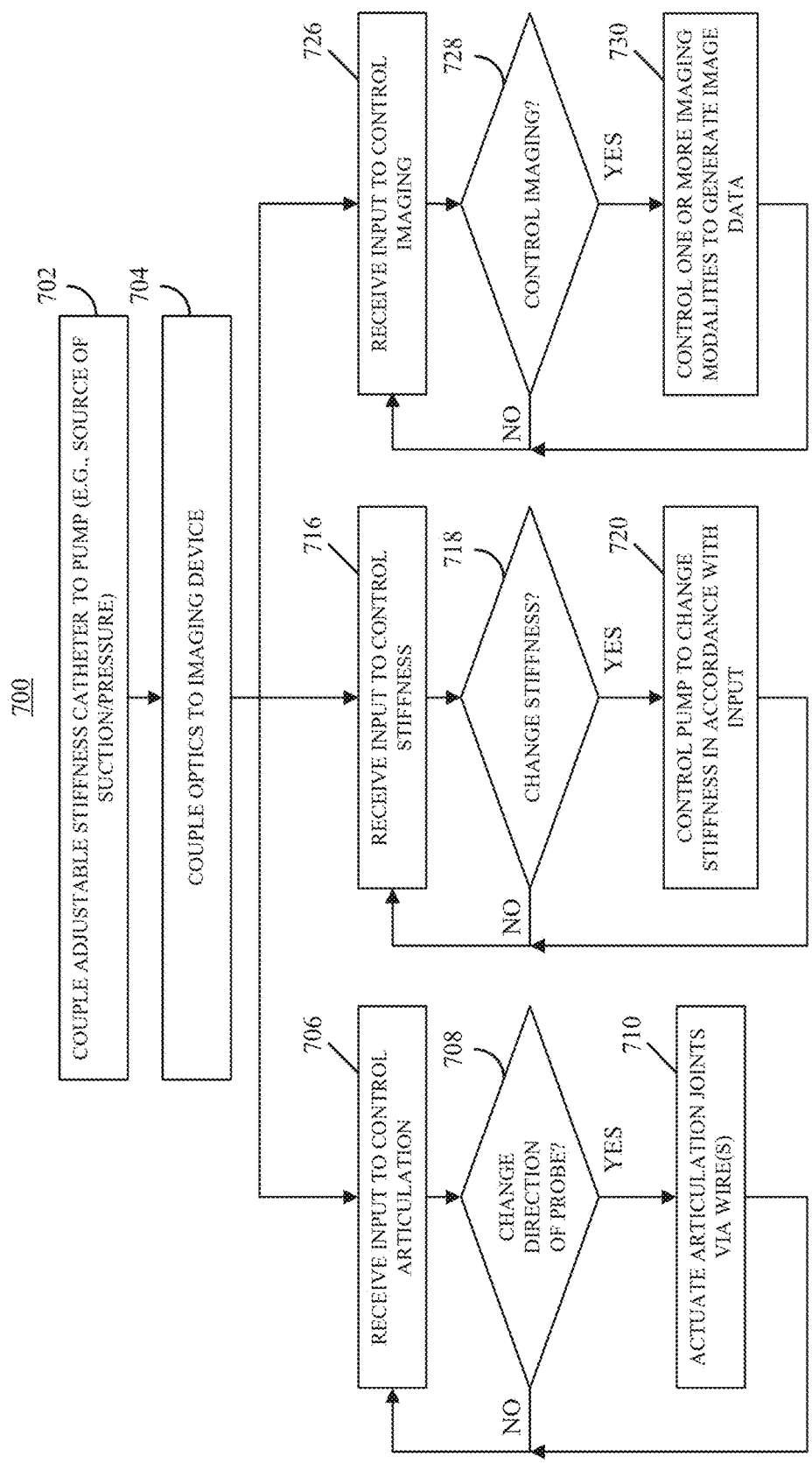
FIG. 7 shows an example of a process for using a variable stiffness and articulating navigation device to position a microendoscope device and generate image data in accordance with some embodiments of the disclosed subject matter.

FIG. 7 shows an example of a process for using a variable stiffness and articulating navigation device to position a microendoscope and generate image data in accordance with some embodiments of the disclosed subject matter. As shown in FIG. 7, at 702, process 700 can include coupling an adjustable stiffness catheter (e.g., catheter 118) to a pump or any other source that can provide variable pressure, such as a syringe.

At 704, process 700 can include coupling optics of the adjustable stiffness catheter (e.g., an optical fiber within tether 102) to an imaging device (e.g., imaging device 402). For example, tether 102 can be coupled to an optical rotatory joint that is coupled via a static optical fiber to imaging device 402. Additionally or alternatively, in some embodiments, process 700 can include completing electrically coupling an imaging device associated with the adjustable stiffness catheter to the imaging device. For example, process 700 can include by coupling a cable associated with digital camera 114 to imaging device 402 (and/to another device, such as computing device 620). As another example, process 700 can include creating a wireless connection between digital camera 114 and imaging device 402 (and/or another device, such as computing device 620).

At 706, process 700 can receive input to control articulation of articulation joints associated with the catheter. For example, a user can provide such input to control the articulation joints via an input device (e.g., a mouse, a keyboard, a touchscreen, a trackball, a joystick, etc.), which can convey the input to control the articulation joints to process 700. In some embodiments, the input to control the articulation joints can be provided electronically (e.g., as an analog signal, as a digital signal, as a wired signal, as a wireless signal, etc.). Additionally or alternatively, in some embodiments, the input to control the articulation joints can be provided mechanically (e.g., by operating a lever, a control wheel, etc.).

At 708, process 700 can determine whether the direction of the probe (e.g., capsule 106) is to be changed by controlling the articulation joints based on the input. If process 700 determines that the direction of the probe is to be changed ("YES" at 708), process 700 can move to 710. At 710, process 700 can actuate the articulation joints via one or more wires (e.g., by driving a linear actuator, by controlling a servo, etc.) to produce the articulation indicated by the input.

Otherwise, if process 700 determines that the direction of the probe is not to be changed ("NO" at 708), process 700 can return to 706 to continue to wait for input.

At 716, process 700 can receive input to control stiffness of the adjustable stiffness catheter. For example, a user can provide such input to control stiffness of the adjustable stiffness catheter via an input device (e.g., a mouse, a keyboard, a touchscreen, a trackball, a joystick, etc.), which can convey the input to control stiffness of the catheter to process 700. In some embodiments, the input can be provided electronically (e.g., as an analog signal, as a digital signal, as a wired signal, as a wireless signal, etc.). Additionally or alternatively, in some embodiments, the input to control stiffness of the catheter can be provided mechanically (e.g., by operating a lever, a control wheel, etc.).

At 718, process 700 can determine whether the stiffness of the catheter (e.g., catheter 118) is to be changed by controlling the pump based on the input. If process 700 determines that the stiffness of the catheter is to be changed ("YES" at 718), process 700 can move to 720. At 720, process 700 can control the pump to increase or decrease pressure in one or more lumens of the catheter to increase or decrease stiffness in accordance with the received input.

Otherwise, if process 700 determines that the stiffness of the catheter is not to be changed ("NO" at 718), process 700 can return to 716 to continue to wait for input.

At 726, process 700 can receive input to control imaging, such as to begin imaging, to stop imaging, to change modes, to adjust one or more imaging parameters, etc. For example, a user can provide such input to control imaging via an input device (e.g., a mouse, a keyboard, a touchscreen, a trackball, a joystick, etc.), which can convey the input to control imaging to process 700. In some embodiments, the input can be provided electronically (e.g., as an analog signal, as a digital signal, as a wired signal, as a wireless signal, etc.). Additionally or alternatively, in some embodiments, the input to control imaging can be provided mechanically (e.g., by operating a lever, a control wheel, etc.).

At 728, process 700 can determine whether one or more imaging modalities (e.g., OCT, confocal microscopy, visible light, etc.) is to the controlled based on the input. If process 700 determines that imaging is to be controlled ("YES" at 728), process 700 can move to 730. At 730, process 700 can change one or more properties and/or states of one or more of the imaging modalities in accordance with the received input.

Otherwise, if process 700 determines that input has not been received to control imaging ("NO" at 728), process 700 can return to 726 to continue to wait for input.

As shown in FIG. 7, controlling the stiffness of the catheter, the shape of the articulation joints, and capturing image data can occur in parallel.

Figures 8A, 8B:
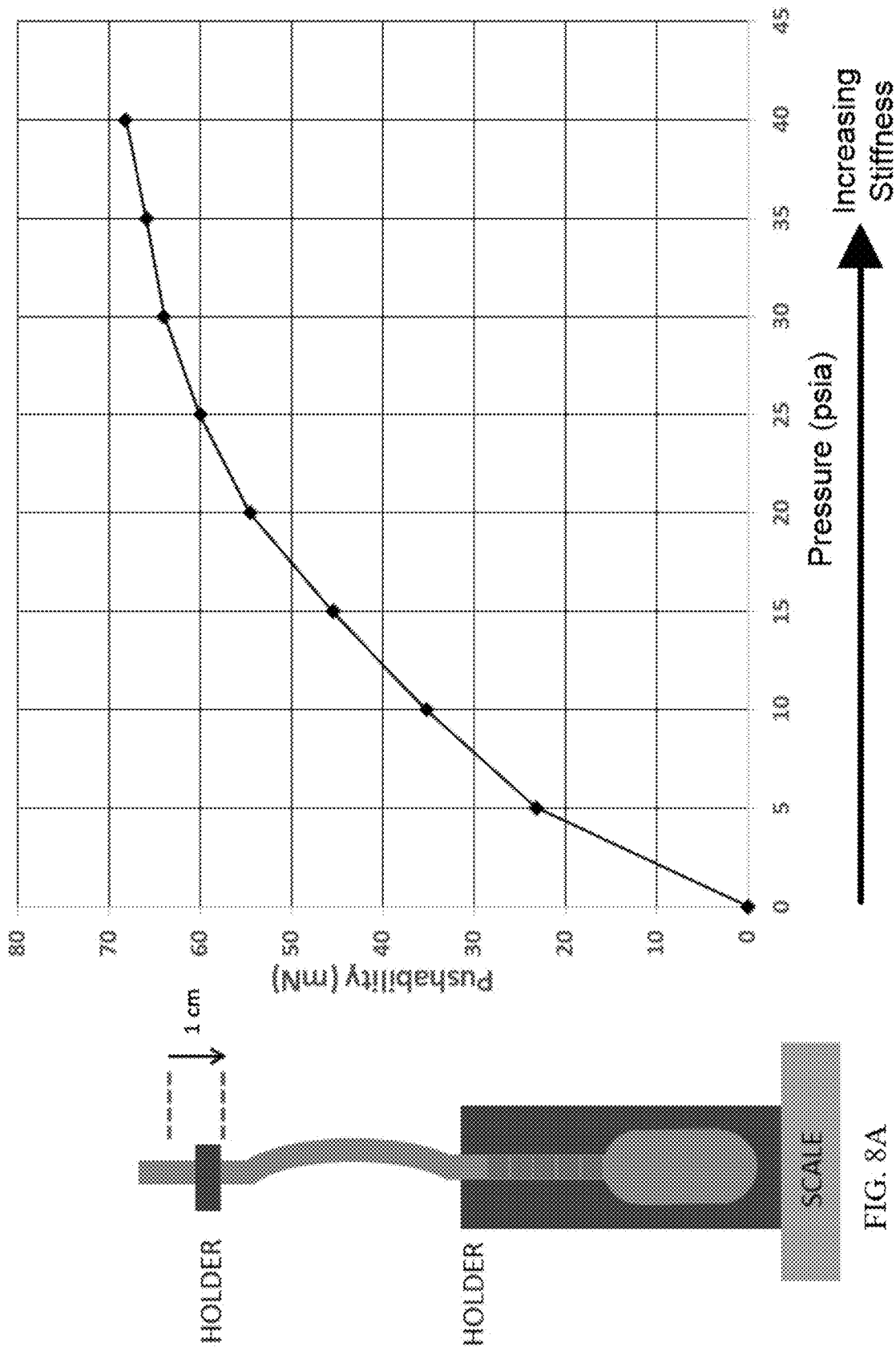
FIG. 8A shows an example of an experimental setup used to measure pushability at various pressures of a variable stiffness catheter implemented in accordance with some embodiment of the disclosed subject matter.
FIG. 8B shows an example chart illustrating measured pushability in millinewtons (mN) at various pressures of a variable stiffness catheter implemented in accordance with some embodiment of the disclosed subject matter.

FIG. 8A shows an example of an experimental setup used to measure pushability at various pressures of a variable stiffness catheter implemented in accordance with some embodiment of the disclosed subject matter. As shown in FIG. 8A, the capsule and articulation joints of a variable stiffness and articulating tethered capsule endomicroscopy device were placed into a holder to immobilize those portions of the device, and a portion of the adjustable stiffness catheter was affixed to another holder. At various internal pressures, the holder affixed to the catheter portion was advanced 1 centimeter (cm) toward the capsule, and the amount of force exerted on a scale was measured.

FIG. 8B shows an example chart illustrating measured pushability in millinewtons (mN) at various pressures of a variable stiffness catheter implemented in accordance with some embodiment of the disclosed subject matter. In particular, the device described below in connection with, and shown in, FIG. 10 was used to generate the measurements shown in FIG. 8B. As shown in FIG. 8B, at atmospheric pressure (i.e., 0 pounds per square inch absolute (psia) in FIG. 8B), essentially none of the force exerted on the tether by advancing the holder 1 cm was transferred to the scale. That is, the force led to deformation of the tether and not to pressure on the capsule/scale. However, as the pressure in the tether was increased, the amount of force transferred to the scale increased. As shown at an internal pressure of about 40 psia, the pushability reached a value of about 68 mN.

Figure 9:
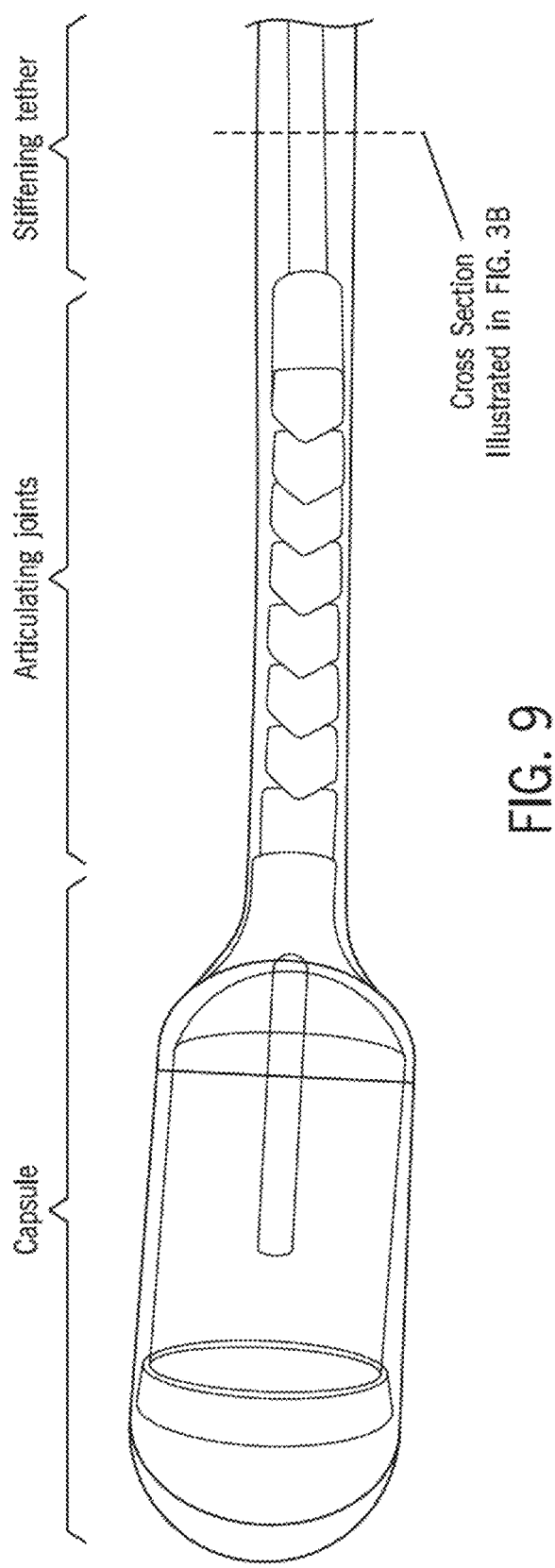
FIG. 9 shows an example of a variable stiffness and articulating tethered capsule endomicroscopy device implemented in accordance with some embodiments of the disclosed subject matter.

FIG. 9 shows an example of a variable stiffness and articulating tethered capsule endomicroscopy device implemented in accordance with some embodiments of the disclosed subject matter. The implementation shown in FIG. 9 includes multiple tubes within the stiffening tether, similar to what is shown in the example of FIG. 3B (where the cross-sectional view of FIG. 3B may correspond to the location indicated by the dashed line in FIG. 9).

Figure 10:
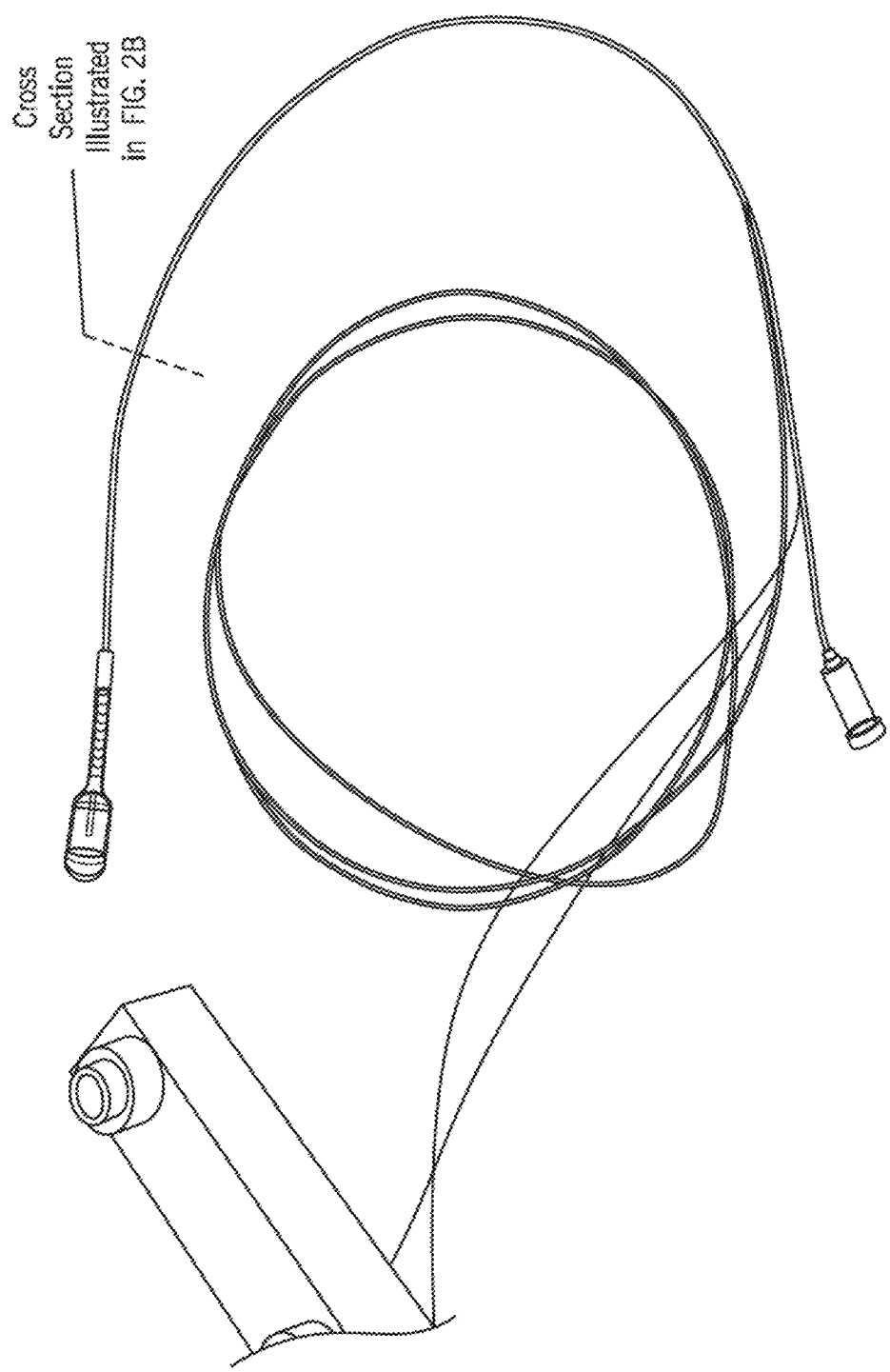
FIG. 10 shows an example of another variable stiffness and articulating tethered capsule endomicroscopy device implemented in accordance with some embodiments of the disclosed subject matter.

FIG. 10 shows an example of another variable stiffness and articulating tethered capsule endomicroscopy device implemented in accordance with some embodiments of the disclosed subject matter. The implementation shown in FIG. 10 includes a single tube surrounding a conventional tether of a tethered capsule, similar to what is shown in the example of FIG. 2B (where the cross-sectional view of FIG. 2B may correspond to the location indicated by the dashed line in FIG. 10).

Figure 11A:
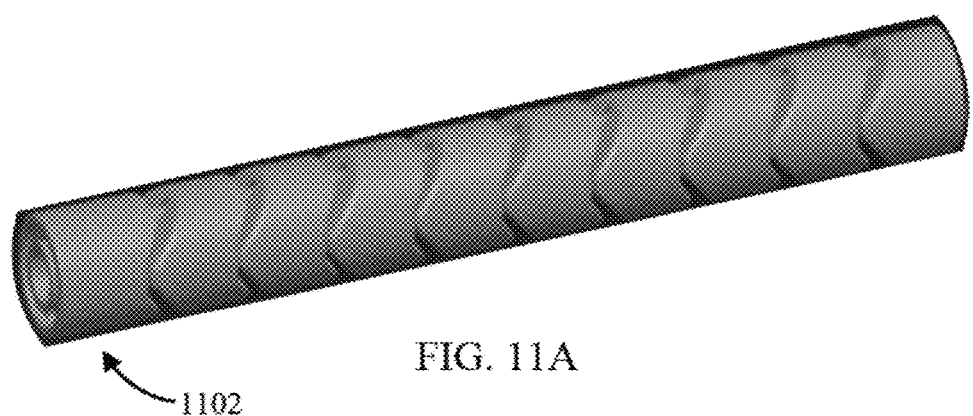
FIG. 11A shows an example of articulation joints that can be used in connection with articulating catheters in accordance with some embodiments of the disclosed subject matter.

FIG. 11A shows an example of articulation joints that can be used in connection with articulating catheters in accordance with some embodiments of the disclosed subject matter. As shown in FIG. 11A, articulation joints can be implemented as multiple cylindrical components that can be nested such that there is space between successive components along two sides (e.g., the top and bottom as shown in FIG. 11A), which can allow the joints to be compressed along one side while expanding along the other. This can be achieved using a wire that passes through each component and is attached to the distal component 1102. By retracting this wire, the distance between the components on the side of the wire decreases, causing articulation in that direction.

Figure 11B:
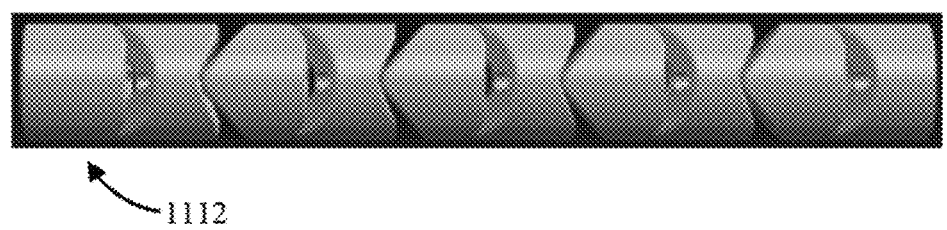
FIG. 11B shows another example of articulation joints that can be used in connection with articulating catheters in accordance with some embodiments of the disclosed subject matter.

FIG. 11B shows another example of articulation joints that can be used in connection with articulating catheters in accordance with some embodiments of the disclosed subject matter. The articulation joints of FIG. 11B are similar to those shown in FIG. 11A, but the direction of the joints alternates (e.g. at 90 degree rotational intervals or at other suitable intervals) to allow for more degrees of freedom.

Figure 11C:
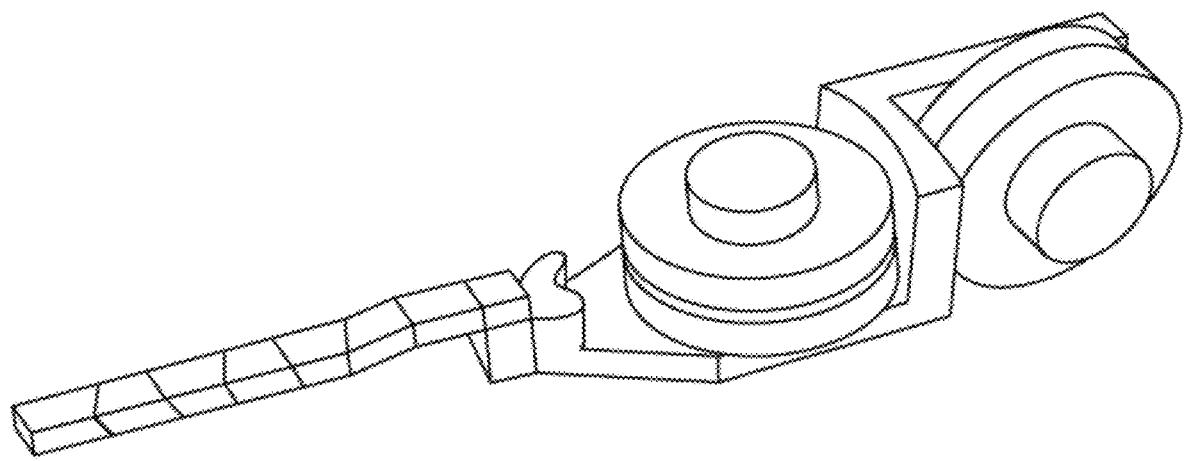
FIG. 11C shows an example of articulation joints that can be used in connection with an articulating catheter implemented in accordance with some embodiments of the disclosed subject matter.

FIG. 11C shows an example of articulation joints that can be used in connection with an articulating catheter implemented in accordance with some embodiments of the disclosed subject matter.

Figure 12A:
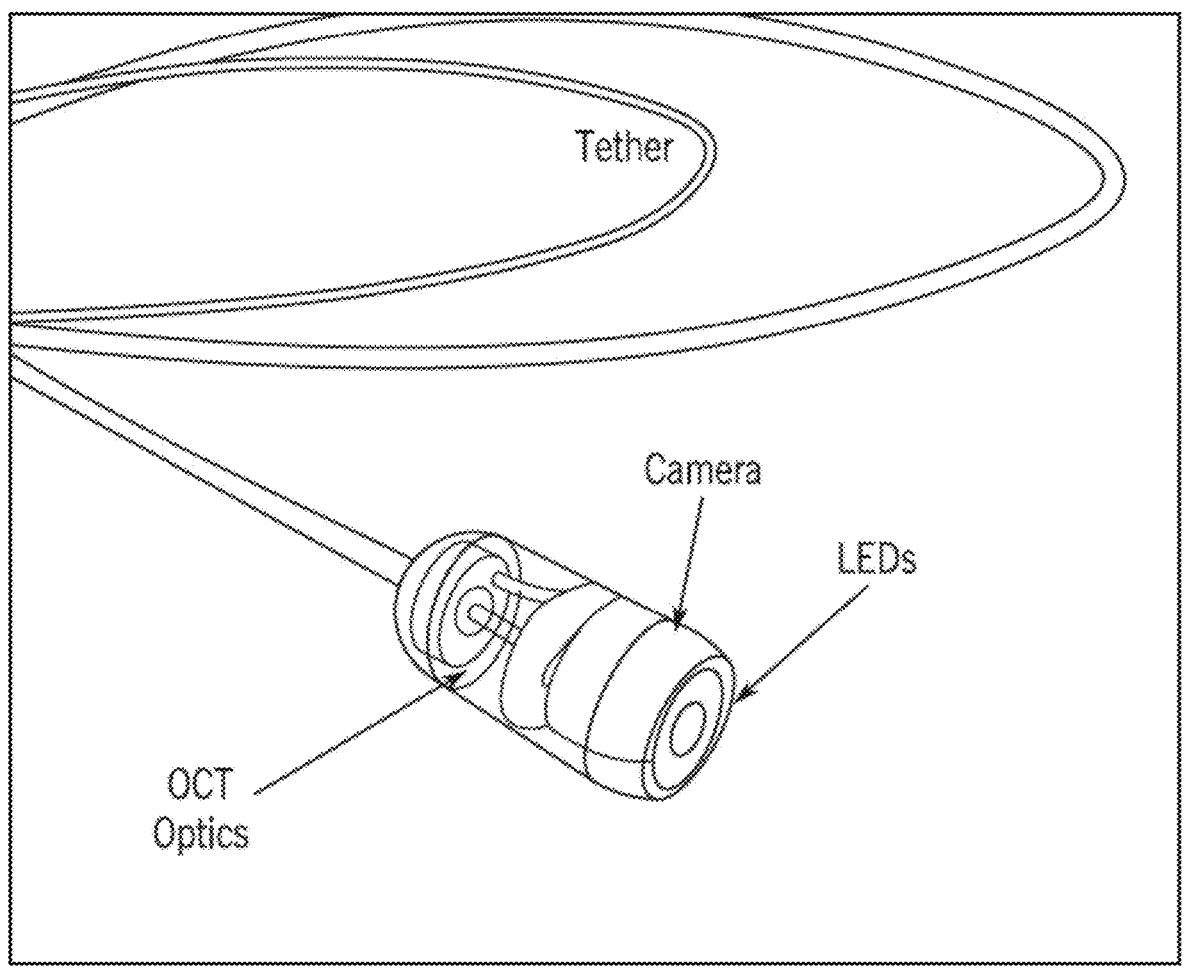
FIG. 12A shows an example of a multimode tethered capsule endomicroscopy device that can be used in connection with variable stiffness and/or articulating catheters in accordance some embodiments of the disclosed subject matter.

FIG. 12A shows an example of a multimode tethered capsule endomicroscopy device that can be used in connection with variable stiffness and/or articulating catheters in accordance some embodiments of the disclosed subject matter. As shown in FIG. 12A, a capsule can include both optics for performing interferometric-type imaging (e.g. OCT imaging), and a digital camera for performing conventional digital imaging. Additionally, LED lights near the distal end of the capsule can illuminate a sample to be imaged using the digital camera. In some embodiments, the digital camera shown in FIG. 12A can be coupled to a computing device electrically (e.g., via wires that run the length of tether 102) and/or wirelessly (e.g., via a transceiver). In some embodiments, a battery can be included within the capsule to provide a source or power to the digital camera and LED lights. Additionally or alternatively, power can be provided via one or more wires that run the length of the tether.

Figure 12B:
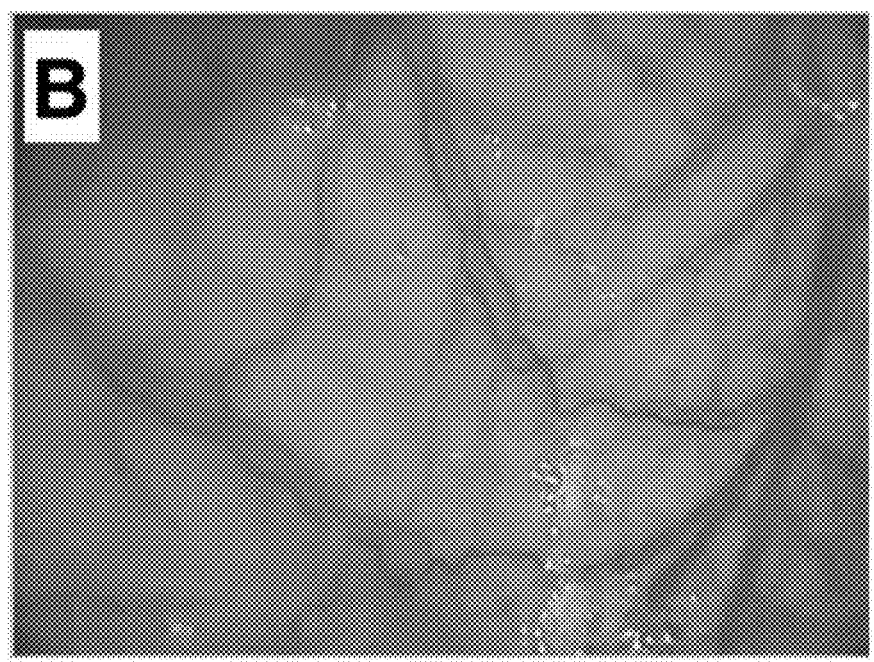
FIG. 12B shows an example of an image of a stomach lining captured with the video camera of a multimode tethered capsule endomicroscopy device.

FIG. 12B shows an example of an image of a stomach lining captured with the video camera of a multimode tethered capsule endomicroscopy device. More particularly, the image in FIG. 12B is an image of the stomach lining of a swine that was captured in vivo using the multimode tethered capsule endomicroscopy device shown in FIG. 12A.

Figure 13A:
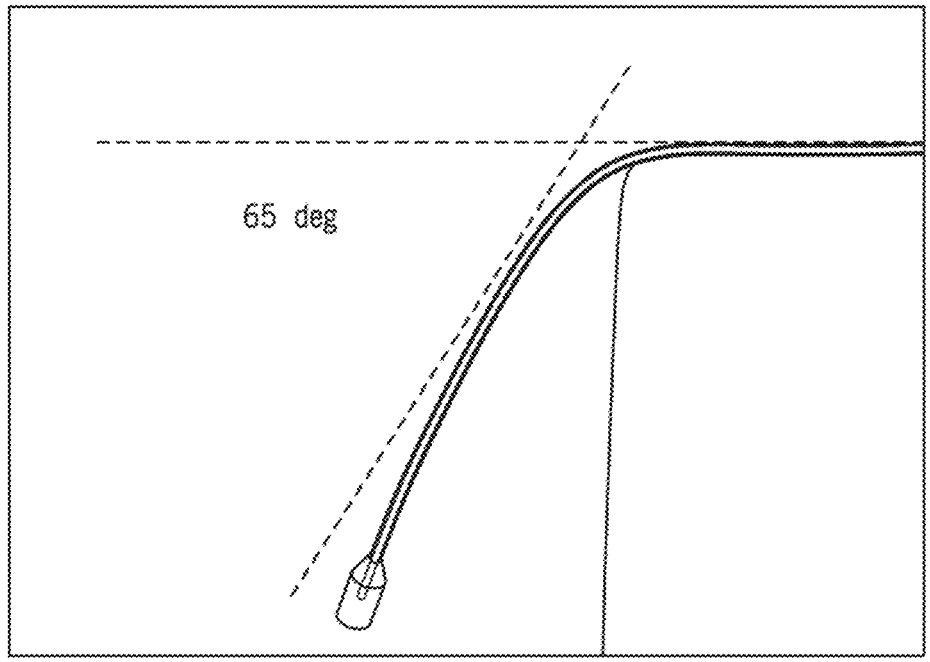
FIG. 13A shows an example of a flexible state of a variable stiffness and articulating tethered capsule endomicroscopy device implemented in accordance with some embodiments of the disclosed subject matter.
Figure 13B:
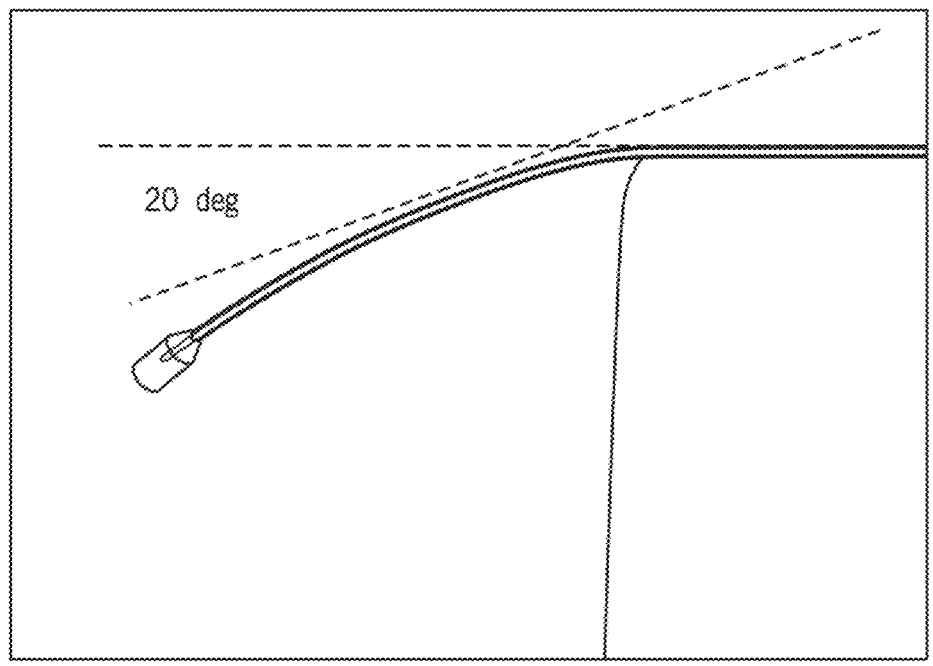
FIG. 13B shows an example of a stiffened state of the variable stiffness and articulating tethered capsule endomicroscopy device of FIG. 13A.

FIGS. 13A and 13B shows examples of a flexible state (resting at an angle of approximately 65 degrees relative to horizontal, FIG. 13A) and a stiffened state (elevated to an angle of approximately 20 degrees relative to horizontal, FIG. 13B) of a variable stiffness and articulating tethered capsule endomicroscopy device implemented in accordance with some embodiments of the disclosed subject matter. As shown in FIGS. 13A and 13B, when the internal pressure within the catheter was increased, the internal force counteracted gravity to an extent.

Figure 14:
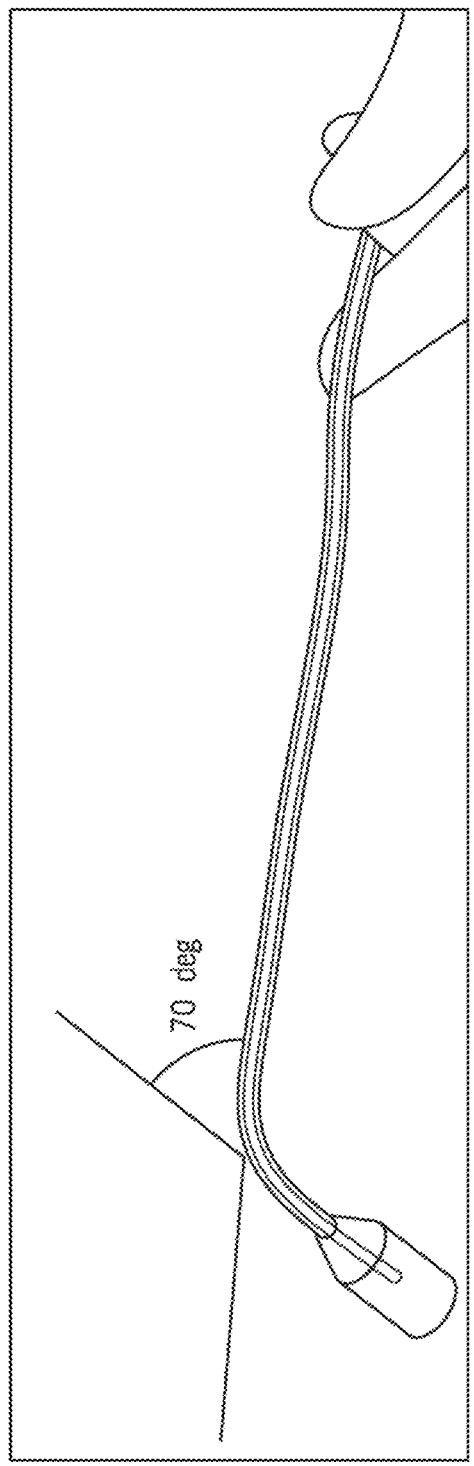
FIG. 14 shows an example of an articulated state of a variable stiffness and articulating tethered capsule endomicroscopy device implemented in accordance with some embodiments of the disclosed subject matter.

FIG. 14 shows an example of an articulated state of a variable stiffness and articulating tethered capsule endomicroscopy device implemented in accordance with some embodiments of the disclosed subject matter. As shown in FIG. 14, articulation joints can be used to point a capsule in a particular direction at an angle of at least 70 degrees compared to the longitudinal axis of the catheter. Note that the catheter in FIG. 14 is in a stiffened state.

Figure 15:
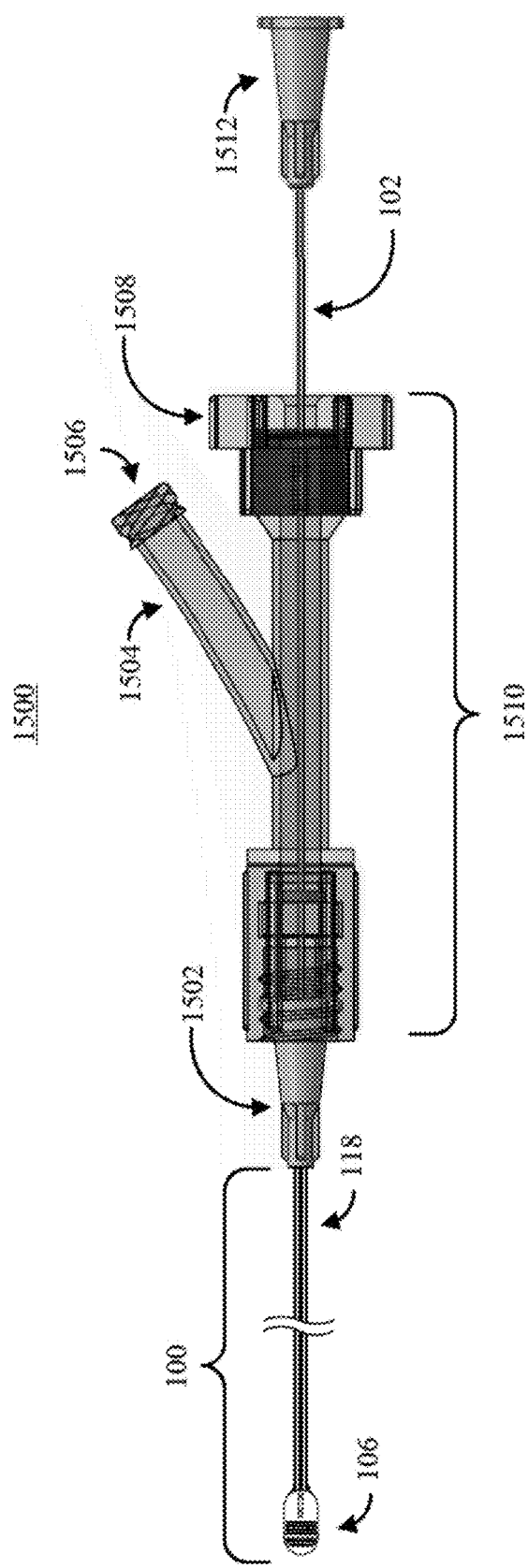
FIG. 15 shows an example of a variable stiffness and articulating tethered capsule endomicroscopy device coupled to a Y adapter that can be used to operatively couple the device to an imaging device and a pump in accordance with some embodiments of the disclosed subject matter.

FIG. 15 shows an example 1500 of an apparatus including a variable stiffness and articulating tethered capsule endomicroscopy device coupled to a Y-adapter that can be used to operatively couple the device to an imaging device and a pump in accordance with some embodiments of the disclosed subject matter. As shown in FIG. 15, apparatus 1500 can include variable stiffness and articulating tethered capsule endomicroscopy device 100 that can be inserted into a subject's body to collect image data. For example, in some embodiments, device 100 can be inserted into the subject's gastrointestinal tract to collect OCT and/or visible light images of the esophagus, stomach, duodenum, etc. As described above, in some embodiments, device 100 can have a relatively small diameter, such that it can be inserted without sedation, for example by instructing the subject to swallow capsule 106.

In some embodiments, a proximal end of catheter 118 can be coupled to and/or include a connector 1502 that is configured to couple device 100 to a housing 1510 using any suitable technique or combination of techniques. For example, connector 1502 can be a Luer-type connector, such as a female Luer fitting that is configured to form a locking Luer connection with a male Luer fitting.

In some embodiments, housing 1510 can include a fitting (e.g., a male Luer fitting) for receiving connector 1502 at a distal end of housing 1510. In some embodiments, housing 1510 can form bore holes through which tubes, gases, liquids, etc., can pass. As shown in FIG. 15, housing 1510 can form a first bore hole passing from the distal end of housing 1510 to a proximal end of housing 1510. Additionally, in some embodiments, housing 1510 may include a Y-adapter (e.g., a hemostatic Y-adapter) which can include an arm 1504 that forms a second bore hole that intersects the first bore hole (or a double Y-adapter that has multiple side arms). In some embodiments, arm 1504 can include a port 1506 that can be configured to be coupled to, for example, tubing to form a conduit for fluid (e.g., gas and/or liquid). As shown in FIG. 15, the first borehole can be co-located with a long axis of housing 1510, and the second borehole can be formed by an off-axis arm; however this is merely an example and housing 1510 and the various boreholes running through housing 1510 can be implemented in various configurations.

In some embodiments, tether 102 can pass through housing 1510 such that it can be coupled an optical rotary junction or an imaging device (or any other suitable device) via an optical connector 1512. In some embodiments, tether 102 can enter housing 1510 through a fluid-tight connector 1508, which prevents fluid from exiting through the back end of housing 1510, which could lead to reduced pressure within catheter 118.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It should be noted that, as used herein, the term mechanism can encompass mechanical components, optics, hardware, software, firmware, or any suitable combination thereof.

It should be understood that the above described steps of the process of FIG. 7 can be executed or performed in any order or sequence not limited to the order and sequence shown and described in the figures. Also, some of the above steps of the processes of FIG. 7 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A method for advancing a capsule endomicroscopy device through a luminal structure, the method comprising:
   providing a capsule endomicroscopy device comprising:
   a tether having a proximal end and a distal end, the tether having a first diameter,
   an optical fiber disposed within the tether, the optical fiber having a proximal end and a distal end,
   a tube enclosing at least a portion of the tether, the tube having a proximal end and a distal end, the tube having a second diameter that is larger than the first diameter,
   a housing coupled to the distal end of the tether and the distal end of the tube, and
   an optical element disposed within the housing and configured to direct light received from the optical fiber toward a periphery of the housing;
   subsequent to the housing entering the luminal structure, causing a first change in pressure within the tube thereby causing a rigidity of the tube to increase;
   pushing the housing through the luminal structure while the rigidity of the tube has increased to advance the housing through the luminal structure; and
   subsequent to pushing the housing, causing a second change in pressure within the tube thereby causing the rigidity of the tube to decrease.

2. The method of claim 1, wherein causing the first change in pressure within the tube further comprises:
   causing the first change in pressure within the tube using a pump coupled to the tube to increase pressure within the tube.

3. The method of claim 2, wherein the tube is a first tube, wherein the capsule endomicroscopy device further comprises a second tube disposed within the first tube, and wherein causing the first change in pressure within the first tube further comprises:
   causing the first change in pressure within the first tube based on using the pump to increase pressure within the second tube.

4. The method of claim 1, wherein free space within the tube is substantially filled by a plurality of individual detached solid particles, and
   wherein causing the first change in pressure within the tube further comprises:
   causing the first change in pressure within the tube based on using a pump to decrease pressure within the tube.

5. The method of claim 1, wherein the tube is a first tube, wherein the capsule endomicroscopy device further comprises a second tube disposed within the first tube and substantially filled by a plurality of individual detached solid particles, and
   wherein causing the first change in pressure within the first tube further comprises:
   causing the first change in pressure within the first tube based on using a pump to decrease pressure within the second tube.

6. The method of claim 1, wherein the capsule endomicroscopy device further comprises a plurality of articulation joint components, wherein:
   each of the plurality of articulation joint components is disposed adjacent to at least one other of the plurality of articulation joints,
   wherein the capsule endomicroscopy device further comprises a wire that passes through the second through hele of each of the plurality of articulation joint components, and wherein the method further comprises:
retracting the wire thereby causing the plurality of articulation joint components to bend the tube and the tether toward the direction of the wire.

7. The method of claim 1, wherein the optical fiber is configured to rotate within the tether and the optical fiber is mechanically coupled to the optical element such that the optical element rotates with rotation of the optical fiber,
wherein the method further comprises:
coupling the tether to an optical rotary joint that causes the optical fiber to rotate within the tether while the housing is being pushed through the luminal structure.

8. The method of claim 1, wherein the luminal structure is a stomach of a subject.

9. The method of claim 1, further comprising:
obtaining structural information from the luminal structure using the optical element, a light source optically coupled to the optical element, and an image sensor optically coupled to the optical element; and
generating optical coherence tomography data of the luminal structure based on obtaining the structural information.

10. The method of claim 1, wherein the second diameter is no greater than two thirds of the first diameter.

* * * * *